(12) United States Patent
Ganem et al.

(10) Patent No.: US 8,464,712 B2
(45) Date of Patent: *Jun. 18, 2013

(54) MEDICATION INHALER

(75) Inventors: Charles F. Ganem, Cape Neddick, ME (US); Jake Ganem, Cape Neddick, ME (US); Scott Ganem, Portsmouth, NH (US)

(73) Assignee: Dose One, LLC, Cape Neddick, ME (US)

( * ) Notice: Subject to any disclaimer, the term of this patent is extended or adjusted under 35 U.S.C. 154(b) by 770 days.

This patent is subject to a terminal disclaimer.

(21) Appl. No.: 12/530,365

(22) PCT Filed: Sep. 7, 2007

(86) PCT No.: PCT/US2007/019596
§ 371 (c)(1),
(2), (4) Date: Sep. 8, 2009

(87) PCT Pub. No.: WO2008/111955
PCT Pub. Date: Sep. 18, 2008

(65) Prior Publication Data
US 2010/0108062 A1      May 6, 2010

Related U.S. Application Data

(63) Continuation-in-part of application No. 11/716,204, filed on Mar. 9, 2007, now Pat. No. 7,832,399.

(60) Provisional application No. 60/781,265, filed on Mar. 10, 2006.

(51) Int. Cl.
*A61M 15/00*           (2006.01)

(52) U.S. Cl.
USPC ............ 128/203.21; 128/203.12; 128/203.15; 128/203.23; 604/58

(58) Field of Classification Search
USPC ............ 128/200.21, 203.12, 203.15, 203.21, 128/203.23, 203.24; 222/80
See application file for complete search history.

(56) References Cited

U.S. PATENT DOCUMENTS

| | | | |
|---|---|---|---|
| 4,014,336 A | * | 3/1977 | Mathes ................... 128/203.15 |
| 4,116,195 A | * | 9/1978 | James ......................... 604/244 |
| 4,338,931 A | | 7/1982 | Cavazza |
| 4,423,724 A | | 1/1984 | Young |
| 5,048,514 A | | 9/1991 | Ramella |

(Continued)

*Primary Examiner* — Justine R Yu
*Assistant Examiner* — LaToya M Louis
(74) *Attorney, Agent, or Firm* — Davis & Bujold, PLLC

(57) ABSTRACT

A medication inhaler comprising an inhaler body, having a medication container chamber for receiving a medication container and an air passage coupling the medication container chamber with exterior air, and a mouthpiece axially engageable with the inhaler body. The mouthpiece has a mouthpiece chamber and a medication delivery needle communicating with the mouthpiece chamber. The needle extends toward the medication container chamber and has an opening for supplying exterior air and medication from an interior cavity of the medication container, accommodated within the medication container chamber, through the needle and to mouthpiece chamber. In the first position, the mouthpiece engages with the inhaler body with such that the needle is spaced from the medication container, and, in the second position, the needle axially traverses the medication container so that the opening in the needle communicates with the air passage and the interior cavity of the medication container to deliver the medication to the patient. The medication inhaler also includes an air bypass which bypasses the needle and supplies supplemental exterior air to the mouthpiece chamber to increase airflow through the medication inhaler.

17 Claims, 19 Drawing Sheets

U.S. PATENT DOCUMENTS

| | | | |
|---|---|---|---|
| 5,263,475 A | 11/1993 | Altermatt et al. | |
| 5,647,349 A | 7/1997 | Ohki et al. | |
| 5,715,811 A | 2/1998 | Ohki et al. | |
| 5,868,721 A | 2/1999 | Marinacci | |
| 5,875,776 A * | 3/1999 | Vaghefi | 128/203.15 |
| 6,159,175 A * | 12/2000 | Strukel et al. | 604/22 |
| 6,488,027 B1 | 12/2002 | Moulin | |
| 6,637,430 B1 | 10/2003 | Voges et al. | |
| 6,766,799 B2 | 7/2004 | Edwards et al. | |
| 6,892,727 B2 | 5/2005 | Myrman | |
| 6,923,175 B2 | 8/2005 | Poole et al. | |
| 6,941,947 B2 | 9/2005 | Young et al. | |
| 6,945,953 B2 | 9/2005 | Wright | |
| 6,983,748 B2 | 1/2006 | Brown et al. | |
| 7,070,583 B1 * | 7/2006 | Higuchi et al. | 604/274 |
| 7,211,062 B2 * | 5/2007 | Kwon | 604/46 |
| 2002/0065492 A1 * | 5/2002 | McGuckin et al. | 604/264 |
| 2003/0187404 A1 * | 10/2003 | Waldenburg | 604/200 |
| 2005/0238708 A1 | 10/2005 | Jones et al. | |
| 2006/0091233 A1 * | 5/2006 | Dutt | 239/88 |
| 2006/0200095 A1 * | 9/2006 | Steube | 604/272 |
| 2006/0254583 A1 * | 11/2006 | Deboeck et al. | 128/203.15 |

\* cited by examiner

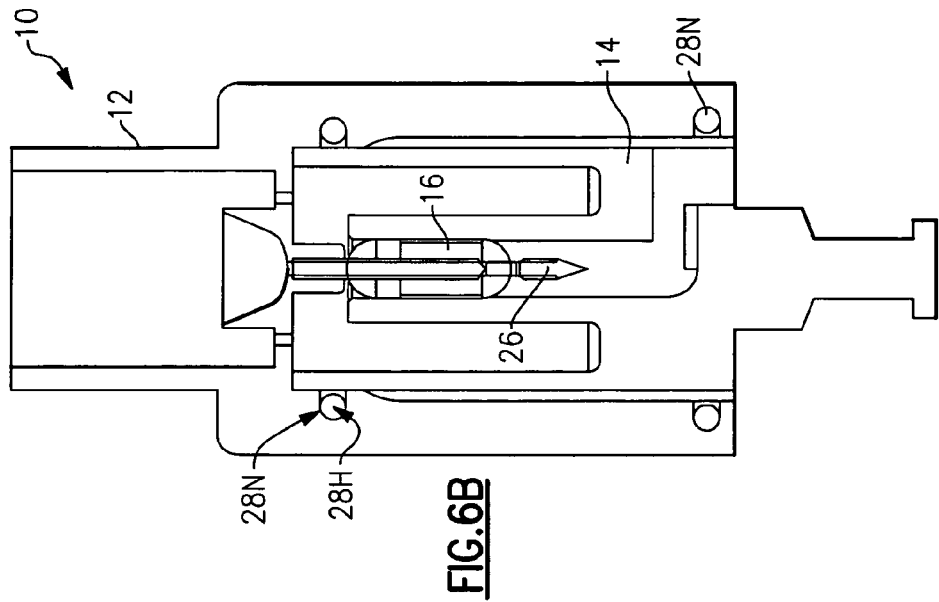
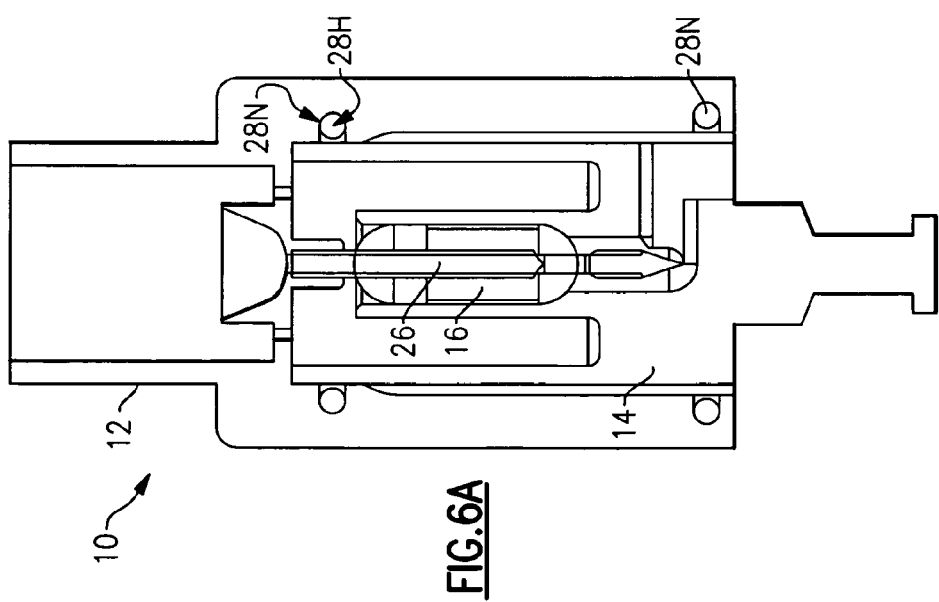

| EMPTY HARD GELETIN CAPSULE PHYSICAL SPECIFICATIONS | | | | |
|---|---|---|---|---|
| SIZE | OUTER DIAMETER (mm) | HEIGHT OR LOCKED LENGTH (mm) | ACTUAL VOLUME (mL) | TYPICAL FILL WEIGHTS (mg) 0.70 POWDER DENSITY |
| 000 | 9.91 | 26.14 | 1.37 | 960 |
| 00 | 8.53 | 23.30 | 0.95 | 665 |
| 0 | 7.65 | 21.70 | 0.68 | 475 |
| 1 | 6.91 | 19.40 | 0.50 | 350 |
| 2 | 6.35 | 18.00 | 0.37 | 260 |
| 3 | 5.82 | 15.90 | 0.30 | 210 |
| 4 | 5.31 | 14.30 | 0.21 | 145 |
| 5 | 4.91 | 11.10 | 0.13 | 90 |

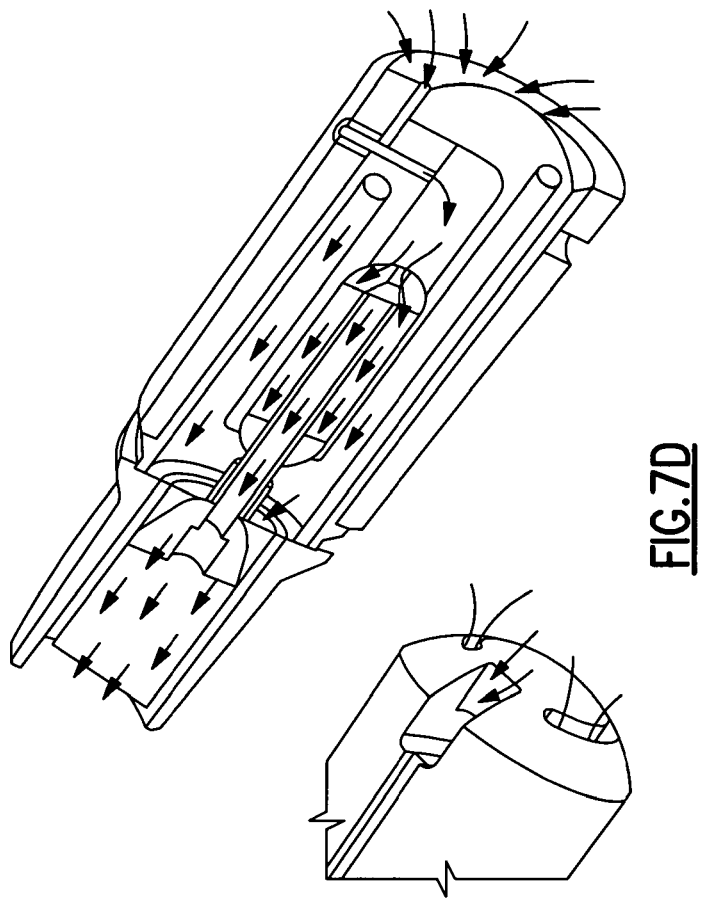
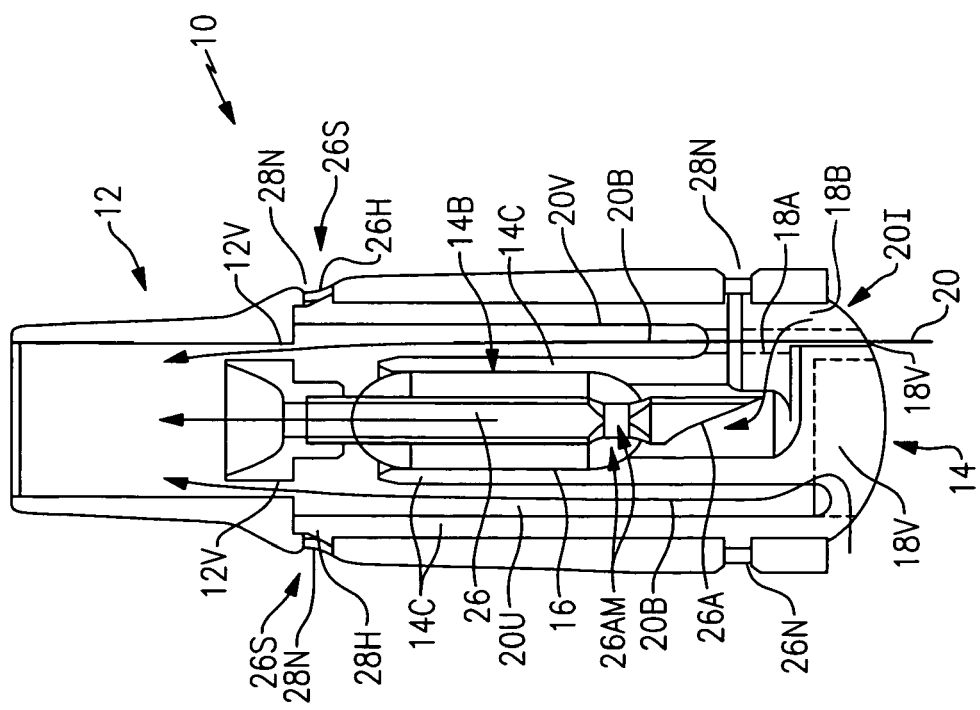
FIG. 7D
FIG. 7C

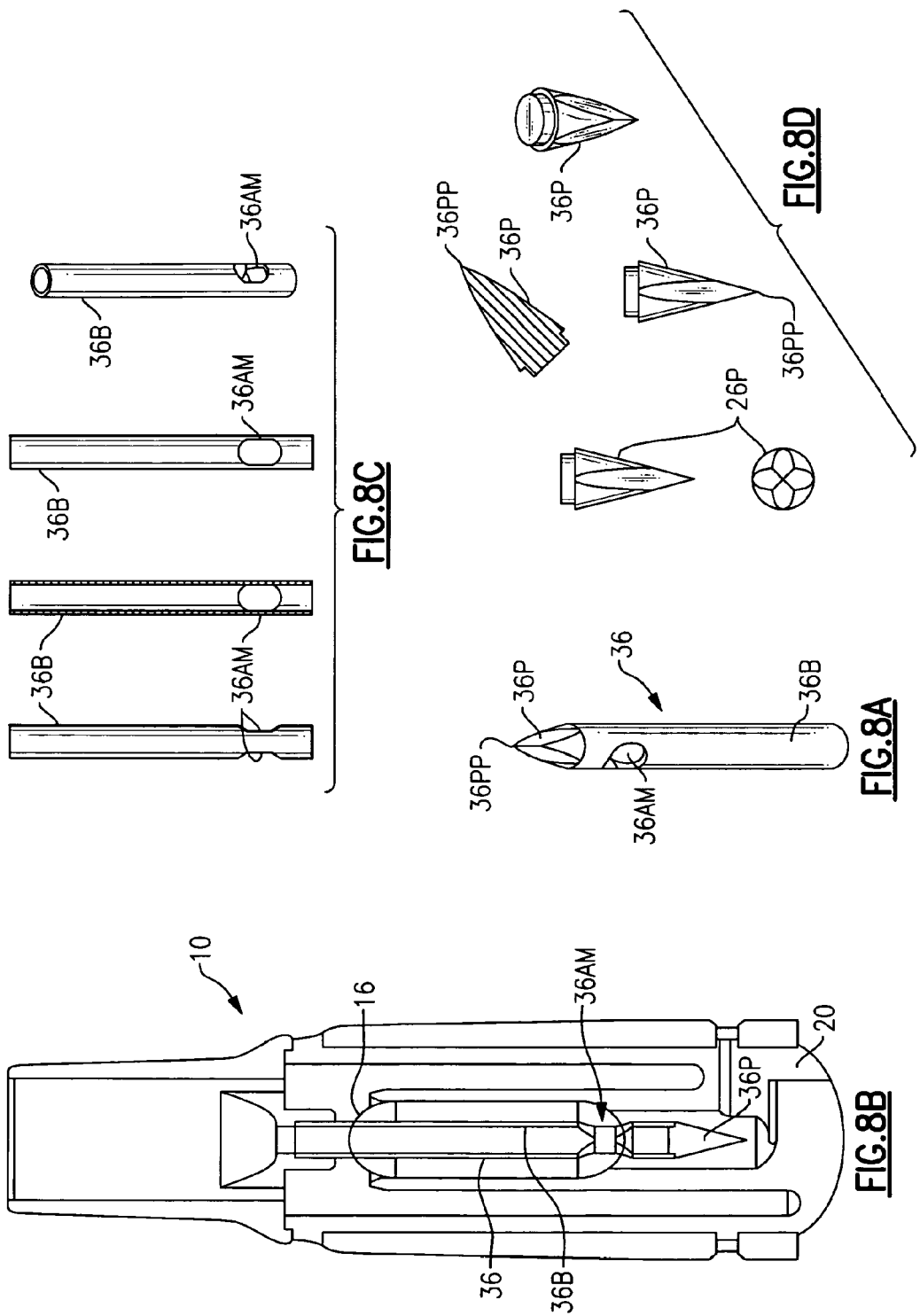

MEDICATION INHALER

This application is a continuation-in-part of and claims benefit of U.S. patent application Ser. No. 11/716,204 filed on Mar. 9, 2007 which is a continuation-in-part of and claims benefit of U.S. Provisional Application Ser. No. 60/781,265 filed on Mar. 10, 2006.

FIELD OF THE INVENTION

The present invention relates to an apparatus for administering medication in the form of a dry powder or a wet medication formulated to as a "dry" medication wherein the medication is formulated to be inhaled and, in particular, to an inhalation dispenser enclosing a sealed capsule of dry powdered or wet medication formulated as a "dry" medication with an air passage mechanism providing access to the capsule contents and an inhalation passage for inhalation of a mixture of air and the dry powder contents of the capsule.

BACKGROUND OF THE INVENTION

There are many medications that are formulated to be inhaled, including medications for respiratory diseases and problems, as such medications are more easily and rapidly absorbed through the respiratory tissues. Such medications are often formulated as "mists", that is, aerosols of droplets suspended in air, but may also be in the form of fine, dry powders.

There are various forms of inhalers designed for the administration of such medications, but each have a number of problems. For example, both wet and dry inhalers must incorporate features that provide safe, long term storage for the medications before they are used, typically by encapsulation of the medications in cartridges or capsules that are loaded into the devices when the medications are to be used. The encapsulated medications must then be "opened" safely and in a manner compatible with the dispensing of the medications, which requires that the medications continue to be retained within the capsule or container, but in such a way as to allow the medication to be dispensed to the patient.

The opening of a medication cartridge or capsule and the extraction of the medication may present particular problems, depending upon the type of medication and the type of cartridge or capsule. For example, cartridges or capsules containing wet medications commonly contain a pressurized propellant. The capsule seal must therefore safely and reliably retain the pressurized contents during storage, which in itself will typically make the seal more difficult to open, and further requires that the capsule seal and the opening mechanism be designed so as to retain the pressurized contents when the seal is breached during the opening process, which present additional difficulties.

Dry medications, however, present a different set of equally difficult requirements and dry powder inhalers of the prior art have employed a number of different types of medication containers, such as blister packs and reservoir storage mechanisms, all of which have been unsatisfactory in one aspect or another. More recent dry powder inhalers of the prior art have employed gelatin capsules, which share certain problems of the other prior art medication containers, such as a tendency for the medications to "clump" and thus be difficult to release from the container, and which present problems particular to gelatin capsules and similar medication containers. For example, one of the major problems of gelatin capsules has been the flaking or shearing of capsule particulate, that is, the production of particles or dust of the capsule material during puncture or destruction of the capsule to gain access to the medication therein. While the capsule material particulate is typically too large to be inhaled into the patient's lungs, the particulate often enters the patient's throat and causes at least some degree of discomfort. This problem is in some respects somewhat analogous to the problem of "coring" in hypodermic needles wherein a hypodermic needle may "core" out a cylinder or plug of tissue when inserted into the body of a patient, rather than opening a passage into the tissue, and wherein as a consequence the freed cored tissue may block the passage through the needle.

For these reasons, among others, inhalers tend to be relatively complex devices that are correspondingly often difficult to use and are generally relatively expensive to manufacture. These characteristics, in turn, largely limit the common use of medication inhalers to regions or countries of relatively high economic and educational levels where they will be administered and used by relatively highly qualified and trained medical personnel and by relatively highly educated patients able to afford and effectively use such devices. There is a significant need, however, for relatively inexpensive, easy to use medication inhalers in economically limited regions of the world and by people, including medical personnel, of relatively low educational levels, and preferably of a single use, throw away form having significantly reduced storage and use requirements.

The present invention addresses these and other associated problems of the prior art.

SUMMARY OF THE INVENTION

The present invention is directed to an apparatus for administering medication in the form of a dry powder or a wet medication formulated to as a "dry" medication wherein the medication is formulated to be inhaled and, in particular, to an inhalation dispenser enclosing a sealed medication container of dry powdered or wet medication formulated as a "dry" medication with an air passage mechanism providing access to the medication container contents and an inhalation passage for inhalation of a mixture of air and the dry powder contents of the medication container.

In particular, the present invention is directed to a dry medication inhaler that includes an inhaler body having a medication container chamber for receiving a medication container and at least one air passage connecting the medication container chamber with exterior air and a mouthpiece axially engageable with the inhaler body and having a mouthpiece chamber for communication with a patient's respiratory system and a hollow medication delivery needle communicating with the mouthpiece chamber. According to the present invention, the medication delivery needle extends toward the medication container chamber and has at least one opening for passing exterior air and medication from an interior cavity of a medication container in the medication container chamber through the needle and to mouthpiece chamber.

The mouthpiece engages with the inhaler body in a first position wherein the needle extends into the medication container chamber short of the medication container in the medication container chamber and in a second position wherein the needle axially traverses the medication container so that the at least one opening in the needle communicates with the at least one air passage and the interior cavity of the capsule or medication container in the medication container chamber.

The dry medication inhaler may also include a detent mechanism for retaining the mouthpiece and the inhaler body in the first position for storing the inhaler with a medication container loaded into the medication container chamber and in the second position when the inhaler is actuated to delivery medication to the patient's respiratory system.

In one embodiment of the present invention, the medication delivery needle is a hollow cylindrical body terminating in a puncture point formed at an end of the needle toward the medication container chamber. A puncture plane extends obliquely across a diameter of the cylindrical body at an end of the needle toward the medication container to define the puncture point at the end of the needle and puncture edges extending along the plane of intersection between the puncture plane and the cylindrical body. The puncture edges form an oval opening into the interior of the needle and include cutting edges extending from the puncture point for a first part of the puncture edges and anti-coring edges for a second part of the puncture edges. When the mouthpiece and inhaler body are moved from the first position to the second position, the puncture point establishes an initial opening through a wall of the medication container, the cutting edges penetrate the wall of the medication container and separate an attached flap of the medication container material from the medication container wall, and the anti-coring edges contact the medication container wall and push the attached flap of the medication container aside, thereby forming an opening through the medication container wall wherein the wall material of the opening remains as a flap attached to the medication container wall.

The medication delivery needle may also have at least one air/medication port located along the medication needle such that when the mouthpiece and inhaler body are in the second position a first portion or part of a length of the air/medication ports is located within the medication container and a second portion or part of the length of the air/medication ports is located in communication with the air passage connecting the medication container chamber with the exterior air. In certain embodiments, the medication needle may have one or more pairs of diametrically opposed air/medication ports.

In further aspects of the invention, the inhaler body may include at least one body vent passage located between the medication container chamber and an outer surface of the inhaler body and connected to the exterior air and the mouthpiece may include at least one mouthpiece passage communicating between the at least one body vent passage and the mouthpiece chamber to provide a flow of exterior air into the mouthpiece chamber.

An embodiment of the medication inhaler includes an inhaler body having a medication container chamber for receiving a medication container and at least one air passage connecting the medication container chamber with exterior air, a mouthpiece axially engageable with the inhaler body and having a mouthpiece chamber for communication with a patient's respiratory system, and a hollow medication delivery needle communicating with the mouthpiece chamber and extending toward the medication container chamber and having at least one opening for passing exterior air and medication, from an interior cavity of a medication container in the medication container chamber, through the needle and to mouthpiece chamber. Again, the mouthpiece engages with the inhaler body in a first position wherein the needle extends into the medication container chamber short of the medication container in the medication container chamber and in a second position wherein the needle axially traverses the medication container so that the at least one opening in the needle communicates with the at least one air passage and the interior cavity of the medication container in the medication container chamber.

In this embodiment, the medication delivery needle includes a hollow, tubular body, a pyramidal puncturing point closing an end of the hollow, tubular body, and a pair of diametrically opposed air/medication ports located along the body so that when the mouthpiece and the inhaler body are moved from the first position to the second position, at least one air/medication port communicates with at least the at least one air passage and at least one air/medication port communicates with at least the interior cavity of the medication container. In addition, the inhaler body and the mouthpiece further include at least one body vent passage located between the medication container chamber and an outer surface of the inhaler body and connected to the exterior air and at least one mouthpiece passage communicating between the at least one body vent passage and the mouthpiece chamber to provide a flow of exterior air into the mouthpiece chamber.

In yet other embodiments of the inhaler of the present invention, the pyramidal point of the needle may be oriented so that diametrically opposed vertices of faces of the pyramidal puncturing point are longitudinally aligned with the pair of air/medication ports, thereby reducing the possibility that the puncture flaps can interfere with the air/mediation ports. In other embodiments the air/medication ports are asymmetrically located along the needle body so that one is primary an inlet port and the other an outlet port.

In still other embodiments, the needle may additionally include a pair of rearward air/medication ports spaced apart from the pair of air/medication ports in a direction away from the puncturing point of the needle to be positioned within the medication container when the mouthpiece engages with the inhaler body in the second position, and a baffle located within the hollow body of the needle between the pair of air/medication ports and the rearward pair of air medication ports.

In yet other embodiments the medication container may include at least one rear vent located at an end of the medication container opposite the puncturing point of the needle, or an exterior diameter of the needle located in a region extending inside and outside a rear wall of the medication container when the mouthpiece engages with the inhaler body may be reduced in diameter to form a rear vent, between the exterior diameter of the needle and the inwardly facing wall of the medication container surrounding an opening by which the needle entered the medication container.

BRIEF DESCRIPTION OF THE DRAWINGS

The above discussed aspects of the prior art and the following discussed aspects of the present invention are illustrated in the figures, wherein:

FIGS. 6A and 6B illustrate adaptations of the inhaler for various sizes of medication containers;

FIGS. 7A-7D are diagrammatic illustrations of an embodiment of the present invention with a first embodiment of a medication delivery needle;

FIGS. 8A-8E illustrate further embodiments of a medication delivery needle and inhaler;

FIG. 17 is a diagrammatic illustration of a basic configuration needle having a reduced rearward circumference to form a rear vent port upon penetration of the medication container by the needle; and.

DETAILED DESCRIPTION OF THE INVENTION

A. General Description of a Dry Medication Inhaler

Figure 1A:
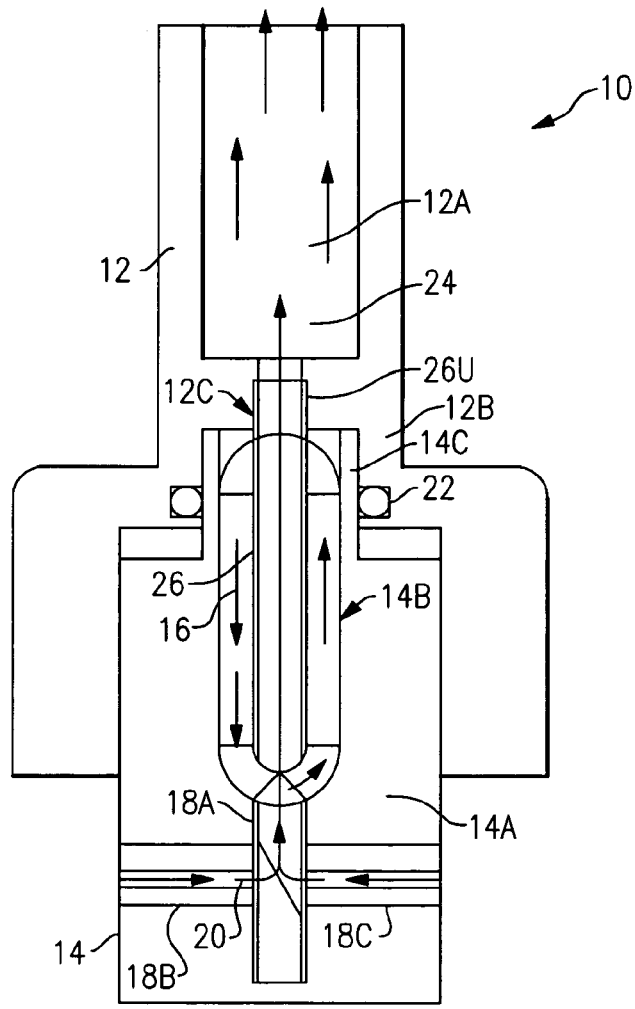
FIG. 1A is a diagrammatic representation of a dry medication inhaler.

Referring to FIG. 1A, therein is shown a diagrammatic representation of a dry medication inhaler 10 according to the present invention wherein, as in all of the following figures unless stated otherwise, references to, for example, the "upper" or "lower" portions of an element will refer to the relative location and orientation of the elements in the Figures.

As represented FIG. 1A, a dry medication inhaler 10 includes a mouthpiece 12 and a body 14 enclosing a medication container 16. In a typical embodiment, the mouthpiece 12 and the body 14 may have, for example, generally cylindrical or oval external transverse cross sections and the exterior cross section of the upper portion of mouthpiece 12 may be further shaped into, for example, a transverse cross section that can be comfortably received by a patient's mouth.

Referring first to body 14, it generally forms a structure for enclosing a medication container 16 and, as shown in FIG. 1A, typically has a cylindrical main body 14A that includes an axially extending container chamber 14B having a length and diameter sized and shaped to closely receive, enclose and accommodate a medication container 16. The body 14 includes one or more air passages for drawing air into and through the medication container 16, which are represented in the figure as including a lower air passage 18A extending downwards from the bottom end of container chamber 14B and intersecting so as to communicate with horizontally extending air passages 18B and 18C that connect with a source of the air exterior to the body 14 to provide a lower air passage 20 extending between the exterior air and into the bottom end of container chamber 14B. It should be noted, however, that the alternate configurations of lower air passages 18A and 20 may be used. For example, there may be only one air passage 18B or 18C intersecting lower air passage 18A or there may be several air passages connecting between the exterior air and the lower air passage 18A rather than just one or two lower air passages 18B/18C. In yet other embodiments, one of more air passages 18B/18C may intersect lower air passage 18A at an angle or slant, rather than at right angles, or lower air passage 18A may extend in a straight path to connect with the exterior air, or lower air passage 18A or one or more air passages 18B/18C may connect with the exterior air through a "torturous", curves and/or zig-zagged path or paths, rather than a straight flow path or paths. In yet other embodiments, the air passage connection between lower air passage 18A and the exterior air may take the form of a slot or slots aligned parallel to, perpendicular to or at an angle or angles with lower air passage 18A, and so on.

In the illustrated embodiment, the body 14 includes a cylindrical wall 14C that surrounds and defines an opening for the container chamber 14B and that extends upwards above the upper end of container chamber 14B wherein, in the illustrated embodiment, the upward extension has an exterior diameter that is less than the exterior diameter of the main part of body 14A. As shown, the interior of cylindrical wall 14C forms an upward end of the container chamber 14B and, as discussed below, cylindrical wall 14C sealingly mates with a corresponding portion of mouthpiece 12. It should be recognized, however, as will be apparent from FIG. 1A and the following descriptions, that the exterior diameter of cylindrical wall 14C may, for example, be equal to that of the main body 14A, with corresponding adaptations to the mating contours of mouthpiece 12.

Referring now to mouthpiece 12, the mouthpiece 12 generally provides a mechanism for opening a medication container 16 residing in the body 14 and for delivering the medication therein to a user. As illustrated in FIG. 1A, the mouthpiece 12 includes two axially connected interior spaces, including a mouthpiece chamber 12A in the upper portion of mouthpiece 12 and a body chamber 12B in the lower portion of mouthpiece 12, with the two chambers being axially connected via a needle passage 12C. As shown, the interior of body chamber 12B and/or the lower part of needle passage 12C are shaped and sized to receive the upper portion of main body 14A and the cylindrical wall 14C, thereby forming an enclosed protective container chamber 14B in which a medication container 16 can be accommodated and reside. The illustrated embodiment of the inhaler 10 may further include a ring seal 22, located in the body chamber 12B that seals against the outer diameter of cylindrical wall 14C to form a single medication passage 24 that extends from lower air passage 20 and through container chamber 14B and any medication container 16 residing therein and needle passage 12C to the mouthpiece chamber 12A. In other embodiments, however, the seal may take the form of a surface to surface contact seal between the corresponding surfaces of the main body 14A and the mouthpiece 12, or a sealing function may not be required.

As also illustrated in FIG. 1A, the mouthpiece 12 includes a hollow medication delivery needle 26 that functions to pierce and/or open the medication container 16, thereby making the medication therein accessible to the patient or the user, and as a delivery mechanism for extracting the medication from the medication container 16 and delivering the medication to the patient or the user. As shown, an upper section of medication delivery needle 16 is fixedly supported by and resides in needle passage 12C with the upper end 26U of medication delivery needle being located in the region of the intersection of needle passage 12C and mouthpiece chamber 12A. As will be shown in following discussions of alternate implementations, the upper end of the delivery needle 26 may be located over an axial range extending from within the needle passage 12C to within mouthpiece chamber. As shown, and as discussed below, the lower end 26L of the medication delivery needle 16 extends downwards to pierce the medication container 16 and to form a flow passage for delivery of the medication when the mouthpiece 12 and the main body 14 are axially moved/telescoped into the activated position.

Figure 1B:
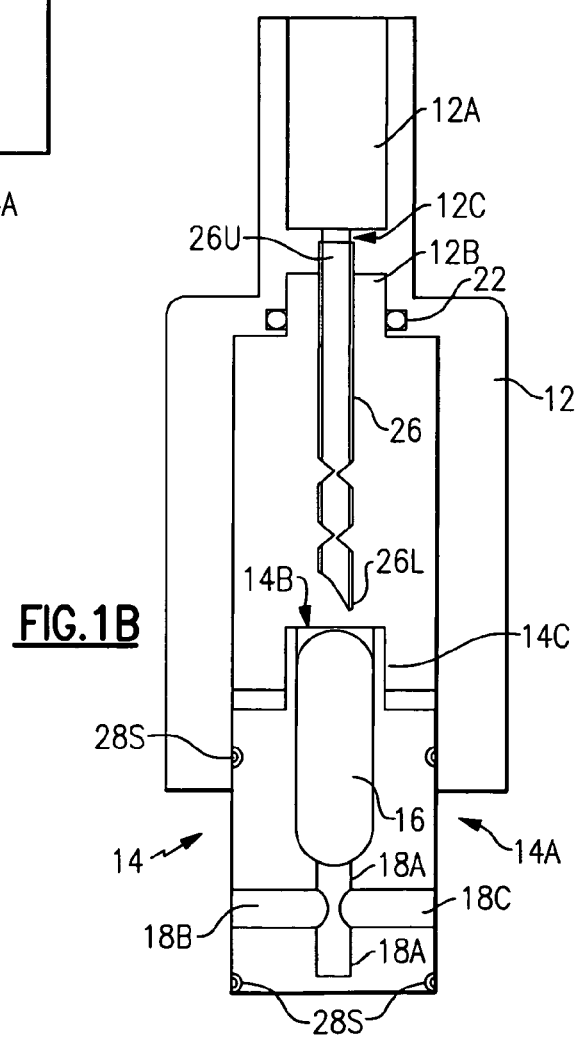
FIGS. 1B and 1C are diagrammatic illustrations of the stored and activated positions of an inhaler.
Figure 1C:
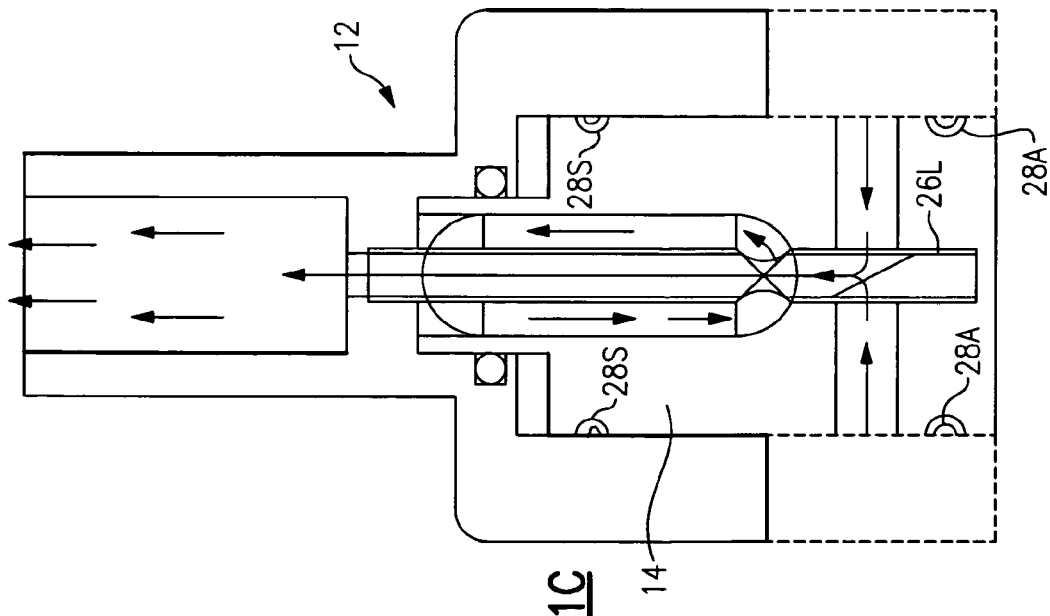

Turning now to use and operation of the medication inhaler 10, and as illustrated in FIGS. 1B and 1C, during an initial step a medication container 16 is inserted into container chamber 14B and thereafter the mouthpiece 12 and main body 14 are fitted together with one another to enclose the medication container 16 (FIG. 1B), whereupon the inhaler 10 is now located in the "storage" state, that is, assembled with a medication container 16 but not yet activated to release the medication from the medication container 16.

When mouthpiece 12 is in the "storage" position with respect to main body 14, that is, when mouthpiece 12 is partially but not fully engaged with main body 14 as illustrated in FIG. 1B, the lower end 26L of delivery needle 26 will extend downwards from the mouthpiece 12 and along the common longitudinal axis of the mouthpiece 12 and the main body 14 to a point short of and spaced slightly from the medication container 16 residing in the container chamber 14B.

At this point, the medical personnel administering the medication to a patient or the patient himself or herself, may activate the inhaler 10, by biasing or pushing the mouthpiece 12 and the main body 14 together toward one another (FIG. 1B) to the fully activated position in order to release and deliver the medication. Once the medication has been administered to the patient, as discussed further below, the inhaler may be opened to remove and discard the expended medication container 16 and the inhaler 10 may be subsequently prepared for another use by inserting a new medication container 16 later use. The inhaler 10 may be thereby employed as a "multi-use device" or, if discarded with the expended container therein after use, as a "single use device," depending upon the particular requirements under which the inhaler 10 is employed.

In the alternative, however, the inhaler 10 can remain in the "storage" state for an extended period of time determined by the packing of the inhaler 10 or the medication container or containers 16 therein, thereby allowing inhalers 10 to be prepared, stored and delivered as pre-loaded ready-to-use devices for delivery of a particular medication. In this regard, it must be noted that medications are typically enclosed in an "overpack", that is, an additional exterior air-tight packaging, to extend the storage life of the medications, and that the useful life of medications, once removed from the overpack, is often limited to 30 days, for example. These methods may be applied to pre-loaded inhalers 10 by, for example, enclosing the pre-loaded inhaler 10 in an overpack or by enclosing the medication containers themselves in individual overpacks within the inhaler 10 whereupon, for example, activation of the inhaler mechanism would both open the overpack as well as the medication container 16.

It should also be noted in this regard that, as will be described further in a following discussion, the mouthpiece 12 may be engaged with the main body 14 and retained in the storage position by, for example, corresponding circumferential detent rings and grooves on the mating respective interior and exterior surfaces of the mouthpiece 12 and the main body 14, or by any other equivalent detent mechanism(s) 28A, 28S. In these implementations, therefore, a positive application of force along the common longitudinal axis of the mouthpiece 12 and the main body 14 would be required to overcome the locking action achieved by the detent so that the mouthpiece 12 can be move so as to be fully engaged with the main body 14 and a medication container 16, residing in container chamber 14B, would remain sealed until such a force was applied.

In this regard it must be noted that a number of alternative implementations may be employed to allow the storage function when the inhaler 10 is to be employed as a pre-loaded ready-to-use device(s). For example, FIG. 1B illustrates an embodiment wherein the portion of the mouthpiece 12 that encloses the main body 14A, when the inhaler 10 is in the "storage" configuration, is extended so that the detent mechanism 28A, located at the lower part of the mouthpiece 12, engages a mating recess 28S in the upper portion of the main body 14 in such a manner that medication delivery needle 26 is held in a "storage" position short of engaging with the medication container 16. In other embodiments, however, the necessary clearance between the medication delivery needle 26 and the medication container 16 may be achieved, for example, by a cylindrical body enclosing either or both of the mouthpiece 12 and the main body 14A and having a detent mechanism or mechanisms interacting with the mouthpiece 12 and the main body 14A.

Now considering activation and an activated state of the inhaler 10, as illustrated in FIG. 1C, the application of a sufficient axial force to the mouthpiece 12 and/or the main body 14 will cause the mouthpiece 12 and the main body 14 to move relative to one another and into the fully activated position. This motion will result in delivery needle 26 being forced through the container chamber 14B, and a medication container 16 residing therein, until the delivery needle 26 extends completely through the container chamber 14B and the medication container 16 and into the lower air passage 18A until the lower end 26L of the delivery needle 26 is located in the lower air passage 18A typically at a location lower than the horizontally extending air passages 18B and 18C.

The inhaler 10 is then located in the fully activated, or engaged, position of the inhaler 10, wherein the medication container 16 is opened, or unsealed, to provide access to the medication contained therein and an air passage is established that extends from the air passage 20 and through the medication container 16, the container chamber 14B and the needle passage 12C and into the mouthpiece chamber 12A.

At this point, it should be noted that the mouthpiece 12 and the main body 14 may include additional corresponding circumferential detent rings, features, recesses, grooves, etc., on their corresponding mating surfaces, or equivalent latching detent mechanisms 28A, to prevent the separation of the mouthpiece 12 from the main body 14 once the inhaler 10 is activated. This feature would prevent refilling and re-use of the inhaler, so that the inhaler 10 would be designed as a single use, throw-away device, which would be particularly useful with relatively untrained or uneducated medical personnel or patients.

Figure 2A:
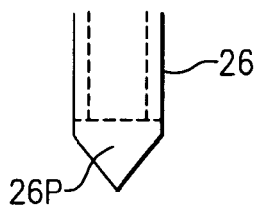
FIGS. 2A-2F are diagrammatic illustrations of possible implementations of a medication delivery needle.
Figure 2B:
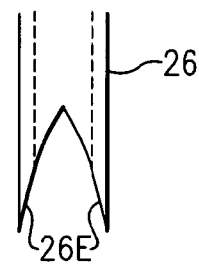
Figure 2C:
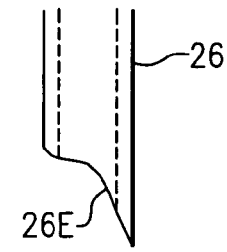
Figure 4:
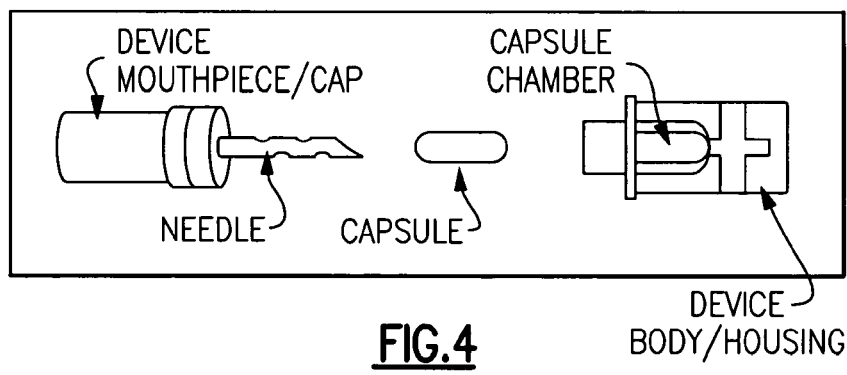
FIG. 4 is a disassembled view of an inhaler.

FIGS. 2A-2D illustrate alternate embodiments of a delivery needle 26 for delivering medication from the medication container 16 to the patient. As shown in FIGS. 2A-2C, the lower end 26L of a delivery needle 26 is shaped to facilitate penetration of the delivery needle 26 into and through the medication container 16 residing in the container space 14B. For example, the lower end 26L may be solid or closed with a sharp, penetrating point 26P or may be shaped into single (FIG. 2C) or double slanting edge 26E (FIG. 2C) terminating in sharp points.

Figure 2F:
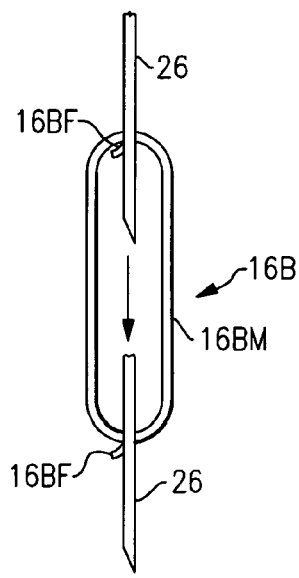
Figure 2D:
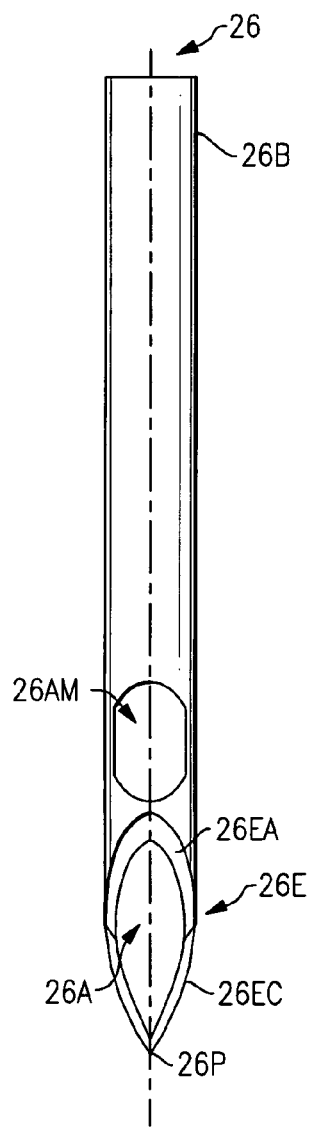
Figure 2E:
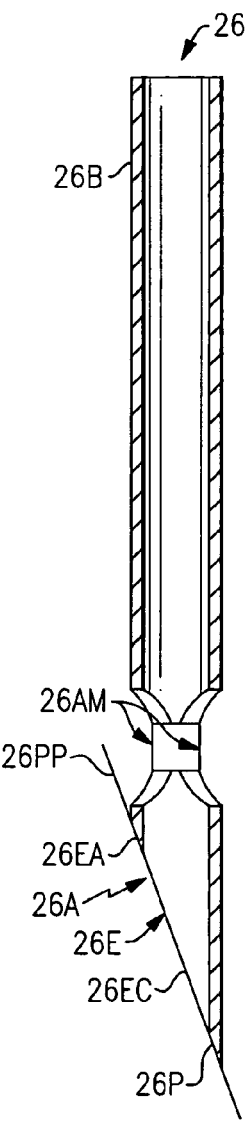

FIGS. 2D and 2E, in turn, illustrates a design for the delivery needle 26 that is particularly adapted to avoid the production of particles or dust for the container material during puncture or piercing of the medication container 16 in order to gain access to the medication contained therein and FIG. 2F illustrates operation of the delivery needle 26 with a medication container 16. As illustrated in FIG. 2D, the delivery needle 26 comprises a hollow generally cylindrical body 26B terminating in a puncture point 26P formed at the leading extreme end of the body 26B by a puncture plane 26PP that extends obliquely, that is, at a slant angle, across the diameter of the body 26B, e.g., at an angle of, for example, approximately 30° to the axis of the body 26B. As shown, the puncture plane 26PP forms a generally oval or elliptically shaped opening which communicates with the interior hollow passage of the needle wherein the edge or the rim of the opening is defined by puncture edges 26E that extend along the intersections between body 26B and puncture plane 26PP from puncture point 26P to a generally diametrically opposite point on body 26B that is located along body 26B at a distance away from puncture point 26P that is compatible with the angle of puncture plane 26PP and the diameter of body 26B.

As indicated in FIGS. 2D and 2E, the puncture edges 26E are formed of cutting edges 26EC that extend from puncture point 26P and along both sides of puncture edge 26E for a desired distance, such as approximately one half the length of puncture edges 26E. Puncture edges 26E then transition into anti-coring edges 26EA that extend along puncture edges 26E from a trailing end of the cutting edges 26EC to the rearmost point of puncture edge 26E, where puncture edges 26E rejoin at the outer surface of body 26B.

In use, and referring to FIGS. 2D, 2E and 2F, the puncture point 26P establishes an initial opening or puncture into the exterior casing or material 16BM of the medication container 16 and the cutting edges 26EC follow the puncture point 26P into material 16BM with a cutting action which begins separation of a flap 16BF from the material 16BM. Separation of the flap 16BF from the material 16BM continues as delivery needle 26 penetrates the material 16BM of the medication container 16, and will continue until anti-coring edges 26EA engage with the material 16BM. At this point, the delivery needle 26 will have cut out a flap 16BF that will form an opening or hole through the material 16BM of the container 16 wall wherein the opening or hole will be of approximately the diameter of the body 16B and will occupy approximately one half to two thirds of the circumference of the body 16B but the flap 16BF will still be attached to the material 16BM of the wall of the container 16.

According to the present invention, anti-coring edges 26EA are formed to have a non-cutting shape, such as a radius rather than a cutting edge, by, for example, grit blasting or polishing or swaging of the anti-coring edges 26EA. As such, the cutting of flap 16BF from the material 16BM of the wall of the container 16 will cease, when anti-coring edges 26EA engage with the material 16BM of the container 16. As such, continued penetration of delivery needle 26 into container 16 will thereby result in the flap 16BF and the material 16BM being pushed aside or otherwise distorted by anti-coring edges 26EA to finish forming the passage through the wall of the container 16 while still leaving the flap 16BF attached to the wall of the container 16.

The above described penetration of the wall of the container 16 and the forming of a hole or passage with an attached flap 16BF will be repeated when the delivery needle 26 reaches and penetrates the opposite wall of the container 16, but with the flap 16BF being formed on the outer side of the container 16 wall rather than on the inner side of the container.

Continuing with alternate embodiments of a delivery needle 26 as illustrated in FIGS. 2A-2C, it will be apparent from the illustrated examples of these embodiments that the basic geometry of the above discussed needle 26, and in particular the configuration of the puncture point or points and various edges, may be configured in a number of ways. It must also be noted that each delivery needle 26 will include at least one air inlet 26A opening for communicating with a corresponding one of air passages 18B and 18C, thereby allowing a passage of exterior air into the interior cavity of the hollow delivery needle 26 and along needle 26 towards the medication container 16 and, eventually, into the mouthpiece chamber 12A and the mouth of the user.

Each delivery needle 26 will further include at least one medication port or inlet 26M in the region of and opening into the interior of the medication container 16 to allow the medication contained within the medication container 16 to be drawn into the interior passage of the delivery needle, together with the exterior air from air inlets 24A, and into the mouthpiece chamber 12A and to the mouth of the user.

In the instance of a medication delivery needle 26 as illustrated in FIGS. 2A-2C, the opening formed by puncture plane 26PP cutting across the diameter of the medication delivery needle 26 to form the puncture point 26P, the puncture plane 26PP, the puncture edges 26E, the cutting edges 26EC and the anti-coring edges 26EA will form the air inlet 26A. A medication delivery needle 26, as illustrated in FIGS. 2A-2C, will also include one or more air/medication ports 26AM along the length of the medication delivery needle 26 spaced from the puncture plane 26PP. As will be described further below, the air/medication ports 26AM may extend on both the inner and the outer sides of the lower opening of the punctured medication container 16, so that each air/medication port 26AM will serve both as an air inlet 26A and a medication inlet 26M.

Figure 3B:
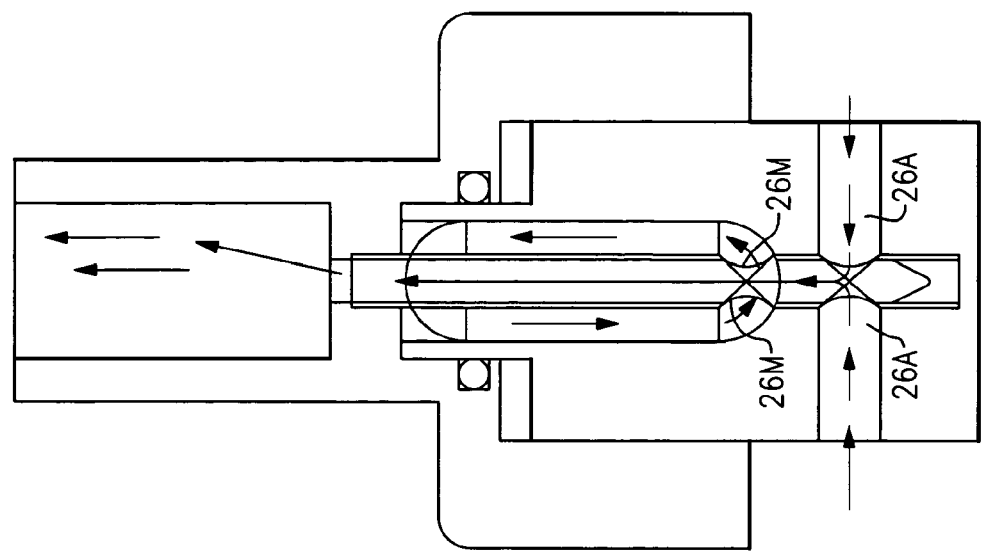
FIGS. 3A-3D are diagrammatic representations of alternate embodiments of a dry medication inhaler.
Figure 3A:
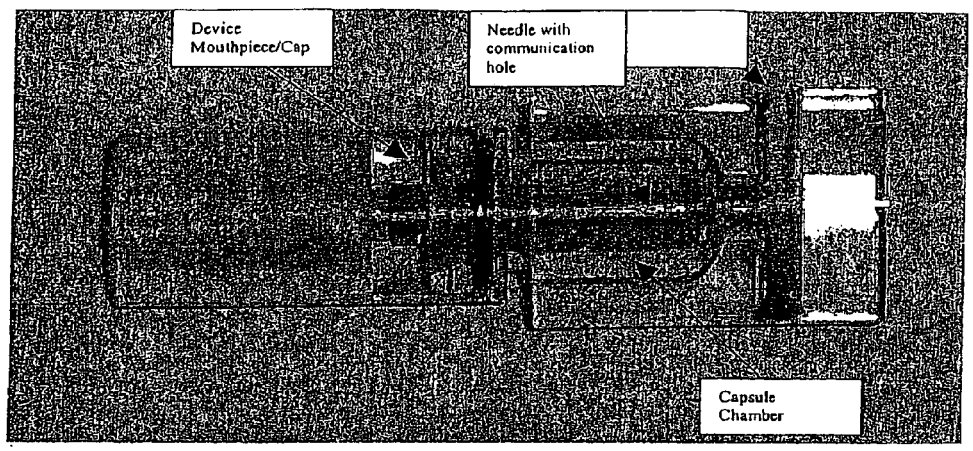
Figure 3D:
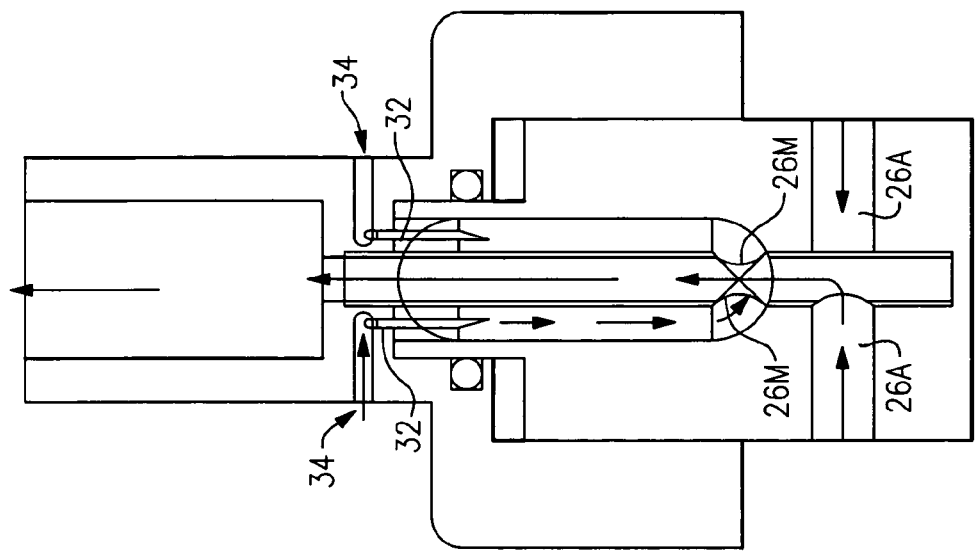
Figure 3C:
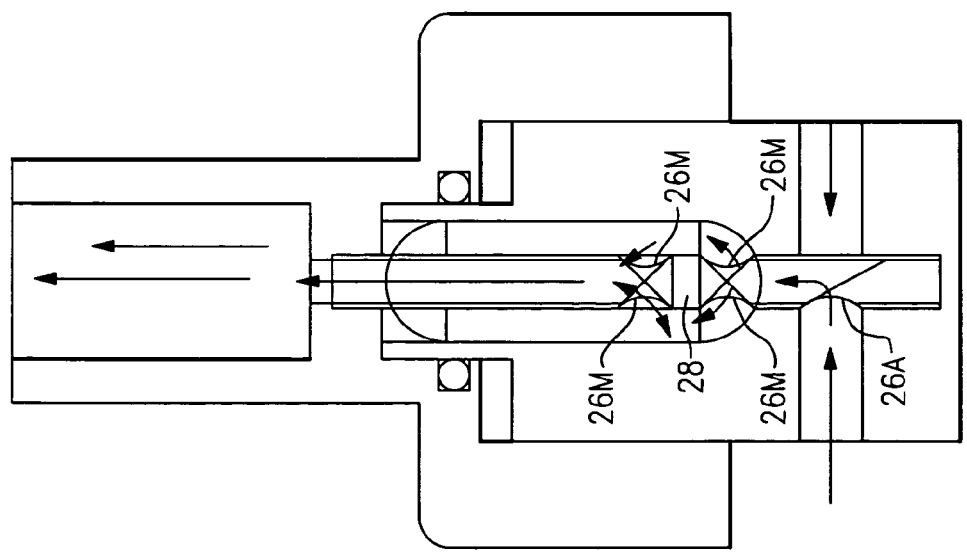

Referring now to FIGS. 3A-3D, FIG. 3A is a view of an assembled inhaler 10 and FIGS. 3B-3D are diagrammatic representations of alternate embodiments of the inhaler 10. FIG. 3B, for example, illustrates an inhaler 10 wherein the delivery needle 26 is provided with a penetrating point 26.

FIG. 3C shows a delivery needle 26 having two vertically spaced pairs of medication ports 26M separated by an intermediate baffle 30 closing the interior passage of the delivery needle 16 between the upper and lower pairs of medication inlets 26M. This design prevents clogging and clumping of the medication, within the medication container 16, by forcing air drawn from air passage 20 and into the lower part of the delivery needle 26 to vent into the interior cavity of the medication container 16, thereby increasing the efficiency of "scouring" of the medication from the medication container 16 by providing a greater pressure differential through the container 16 and thus a greater volume of air flow. Depending upon the type and composition of the medication contained in the medication container 16, this design may also provide a "stirring" of the medication therein before transporting the medication out of the medication container 16 through the upper pair of medication ports 26M and through the needle 26 to the mouthpiece chamber 12A, thereby reducing the possibility of "clogging" or trapping of the medication in the container 16 or the flow passages.

FIG. 3D, in turn, illustrates an embodiment of an inhaler 10 that addresses the same approaches as the embodiment of FIG. 3C, but in a different form. In the embodiment of FIG. 3D, and in addition to medication needle 26, which may include one or more air/medication ports 26AM, the lower part of the mouthpiece 12 that abuts against the main body 14 and, in particular, container chamber 14C, supports one or more hollow secondary needles 32 that connect and communicate with exterior air through corresponding secondary air passages 34 and that extend into container chamber 16. When the mouthpiece 12 and the main body 14 are moved into the activated position, the secondary needles 32 penetrate the medication container 16 so that air can be drawn, through the secondary air passages 34 formed by the secondary needles 32, and into the upper part of the medication container 16 when the user draws on mouthpiece 12. The resulting flow of air into the upper part of the medication container 16 and downwards and out through medication inlets 26M will assist in preventing clogging and clumping of the medication and will further assist in carrying the medication out of the medication container 16 and along the needle 26 to mouthpiece chamber 12A. It will be understood by those of ordinary skill in the relevant arts that the diameters of the secondary needles 32 and the primary needle 26 and of the various size and location of the air and medication ports and passages must be selected in consideration of the suction that can be comfortable exerted on the mouthpiece 12 by a patient, the air flow necessary to move the medication to the patient, and the desired rates and proportions of air and medication flows through the inhaler 10.

It will be understood that the inhaler 10 of the present invention, including the mouthpiece 12, the main body 14A and the medication delivery needle 26, may be constructed of any of a range of materials suitable to their intended purposes, such as glass, metal, plastics, ceramics, etc. It will also be understood that the term "container" used in the above description, such as the medication container 16, is used in the generic sense and general means a container for medication, rather than in a specific and limiting sense. It will be apparent from the above discussion that a "container" as the term is used herein and in the claims may assume any of a variety of shapes other than the generally oval capsule shown herein for illustrative purposes, such as a blister pack, and that the container may be made of any of a wide range of materials. It must also be understood that the specific shapes, proportions and/or dimensions of the various elements of the inhaler 10 will be at least in part dependent upon the constitution of the medications to be dispensed. In the case of dry medications, for example, some medications comprise pure medication, often being "snowflake-like" particles, while others comprise particles of medication attached to particles of a carrier material, all of which may affect the materials and/or dimensions of a specific design of an inhaler 10.

In further examples, of alternate embodiments or features, the delivery needle 26 may extend into mouthpiece chamber 12A, or the entry of needle passage 12C may be surrounded by a cylindrical baffle, to direct the flow of air and medication from the needle passage 12C towards the mouthpiece outlet to the user, thereby assisting in preventing clumping and clogging and the deposition of the medication on the inner surfaces of the mouthpiece chamber 12A. The circumference of the lower part of mouthpiece chamber 12A may also include additional air inlets for the same purpose, that is, the creation of air currents to direct the mixture of air and medication as desired.

Figure 5:
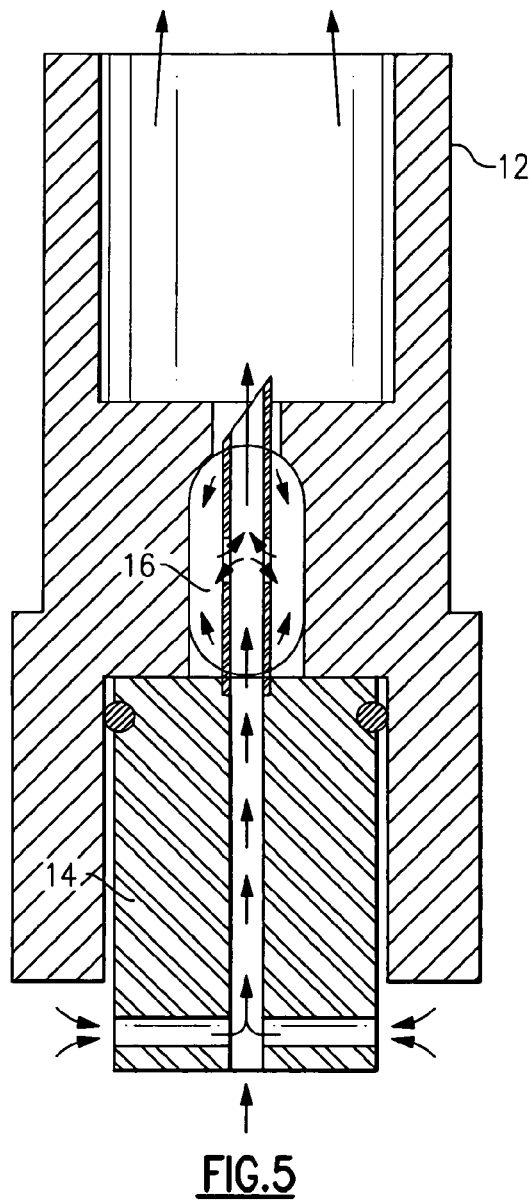
FIG. 5 is a diagrammatic representation of an alternate embodiment of a dry medication inhaler in which the roles of the mouthpiece and body are reversed with respect to the location and operation of the medication delivery needle.

Yet another alternate embodiment is illustrated in FIG. 5, which is a diagrammatic representation of an alternate embodiment of a dry medication inhaler in which the roles of the mouthpiece and the body are reversed with respect to the location and the operation of the medication delivery needle.

It should also be noted that while an inhaler 10 of the present invention is generally intended for use with dry medications, it is possible to use the inhaler of the present invention with, for example, a "dry" medication comprising a "wet" medication retained in the container in, for example, an air gel or other absorbent or micro-pore material, or semi-solid medications, either of which would be delivered by evaporation or sublimation into the air flowing through the medication container. In this sense, therefore, the term "dry" medication includes medications that are "wet" but not liquid in the sense of a substance that will readily flow.

In still further examples of possible implementations of the present invention, an inhaler 10 is described herein above as a single-container single-use device, as a single-container multi-use device, and as a pre-loaded ready-to-use device. In yet other embodiments, the inhaler 10 may be implemented as a "multi-shot" device wherein, for example, the main body 14 is provided with multiple container chambers 14B that can be selected by, for example, rotating or sliding the main body 14A, or with a single container chamber 14B and a rotary or sliding magazine for loading successive medication containers 16 into the container chamber 14B.

B. Effects of Container Size on Embodiments

As described briefly above, the medication containers 16 may differ significantly in size, that is, length, width and/or capacity, as well as shape and in the materials from which they are manufactured. Examples of the dimensions of typical capsules are illustrated in FIG. 6C.

Figure 6C:
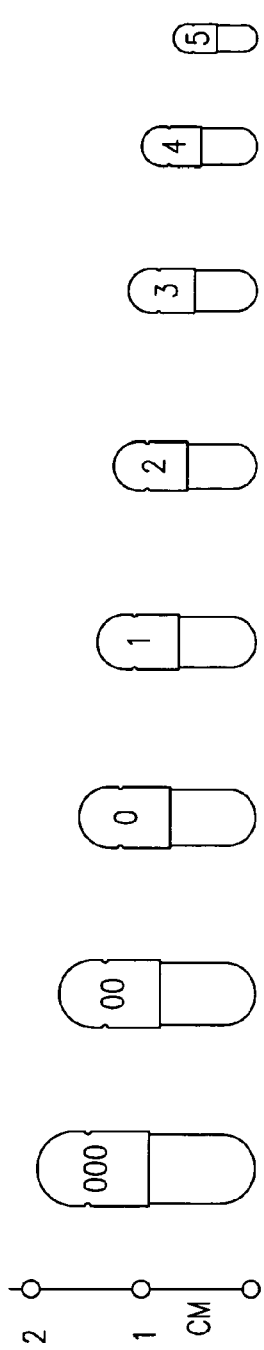
FIG. 6C is a table illustrating capsules having various sizes and capacities.

As shown, FIG. 6A illustrates a larger capacity capsule and FIG. 6B illustrates a smaller capacity capsule, the adaptation of a dry inhaler 10 of the present invention to containers of different capacities, dimensions and/or shapes often requires only changes in the internal dimensions of the container chamber 14C and a possible change in the diameter of delivery needle 26 so that the diameter of delivery needle 26 is compatible with the diameter of the medication container 16. The overall external configuration and dimensions of the inhaler 10, however, may remain the same for a wide range of embodiments for different container capacities, dimensions and/or shapes, examples of which are illustrated in FIG. 6C. It should be noted, however, that the external configuration or dimensions of a given embodiment of an inhaler 10, or a portion thereof, could be varied to provide, for example, a visual or tactile differentiation between inhalers 10 loaded with different medications or dosages or with medication containers other than capsules.

In this regard, it must be recognized and understood that while the inhaler 10 of the present invention is generally illustrated and described herein in terms of medication containers 16 in the form of gelatin capsules, other forms of the medication containers 16 may be used readily and with equal facility in an inhaler 10 of the present invention. For example, the medication containers 16 may comprise blister type packages or other forms of molded containers or that, for example, the medication could be formed into a frangible container or pellet, so that the medication effectively forms its own container. In this instance, for example, the container chamber 14B would effectively form the outer encapsulation of the medication container and would retain the medication in both its sold form and in its powdered form after it had been crushed or pierced by the needle.

C. Alternate Needle Configurations

It will be understood, as discussed above, that the dimensions and configuration and/or shape of at least certain of the inhaler 10 components, such as the diameter and the lengths of the mouthpiece 12, the body 14, the container chamber 14B and the medication delivery needle 26 will be dictated largely by the dimensions of the medication containers 16 and the inherent requirements for transporting the medications from the medication container to the patent. It will be apparent that other factors dictating or influencing the dimensions and configurations of the inhaler 10 components and assembly will include, for example, the requirements of a patient or other person loading and using the inhaler 10 and possible adaptations of the inhaler 10 components and assembly, for example, the automated manufacture and assembly of the components, including the assembly and loading of pre-loaded inhalers 10.

In this regard, it must be understood that the shape, configuration and/or dimensions of the medication delivery needle 26 will have a significant effect on such factors as how the needle 26 penetrates or pierces and "opens" the medication container 16 and how the medication therein is transported from the medication container 16 to the patient by the air flow through the medication container 16 and the needle 26. For these reasons, therefore, the following will discuss various embodiments and variations of the medication delivery needle 26 and other related aspects of the inhaler 10.

Referring first to FIGS. 7A-7D, these figures shown diagrammatic illustrations of an embodiment of a dry inhaler 10 of the present invention and an implementation of the medication delivery needle 26 as employed therein. It will be seen from FIGS. 7A-7D that the component parts, configuration and/or structure of the inhaler 10, represented therein, correspond generally to those discussed herein above with respect to FIGS. 1A-1C, 3A-3C, 4 and 5, for example, and that the shape, configuration and/or operation of the medication delivery needle 26 correspond generally to the medication delivery needle 26 described, for example, in FIGS. 2D-2E.

Figure 7A:
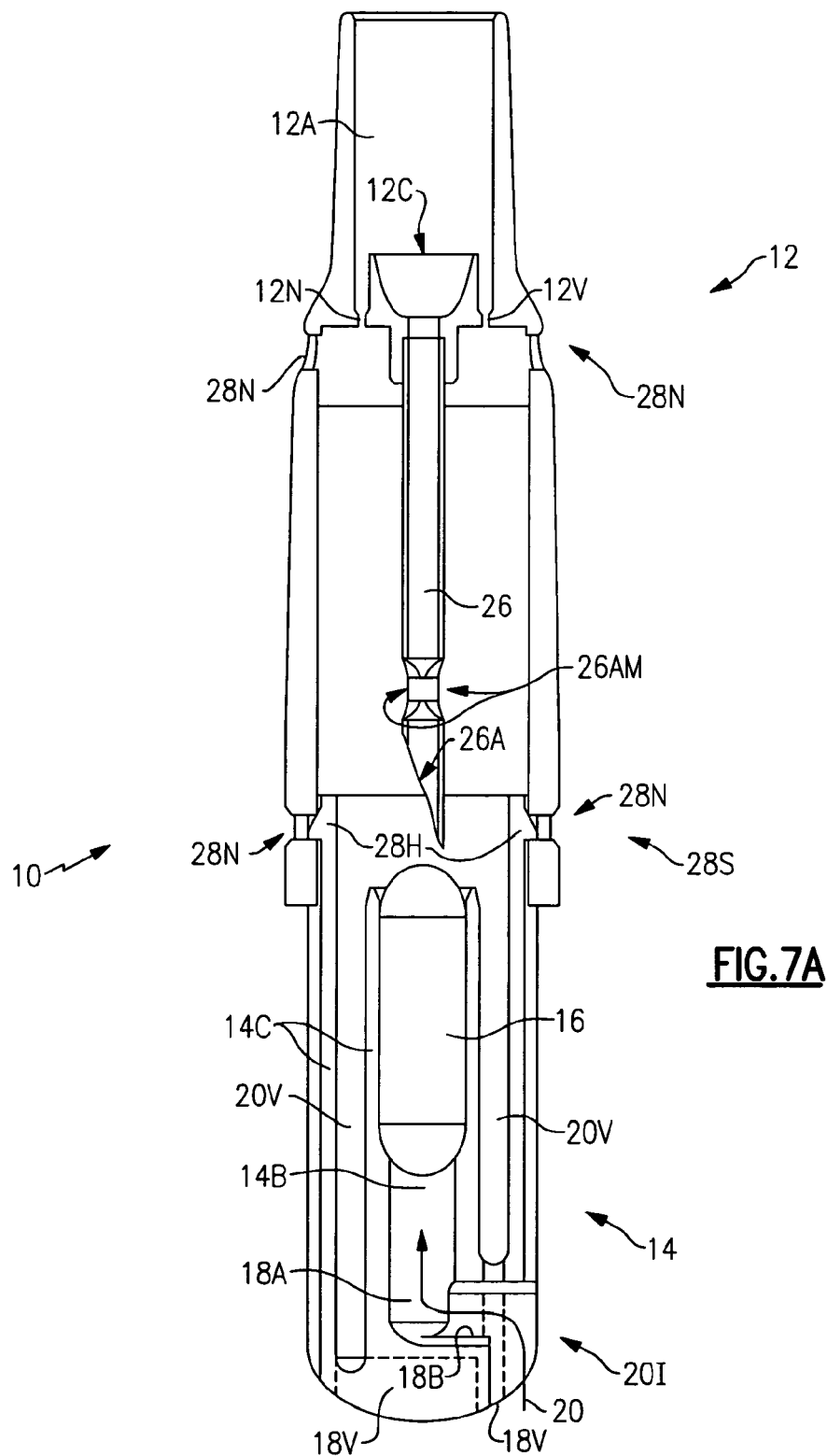
Figure 7B:
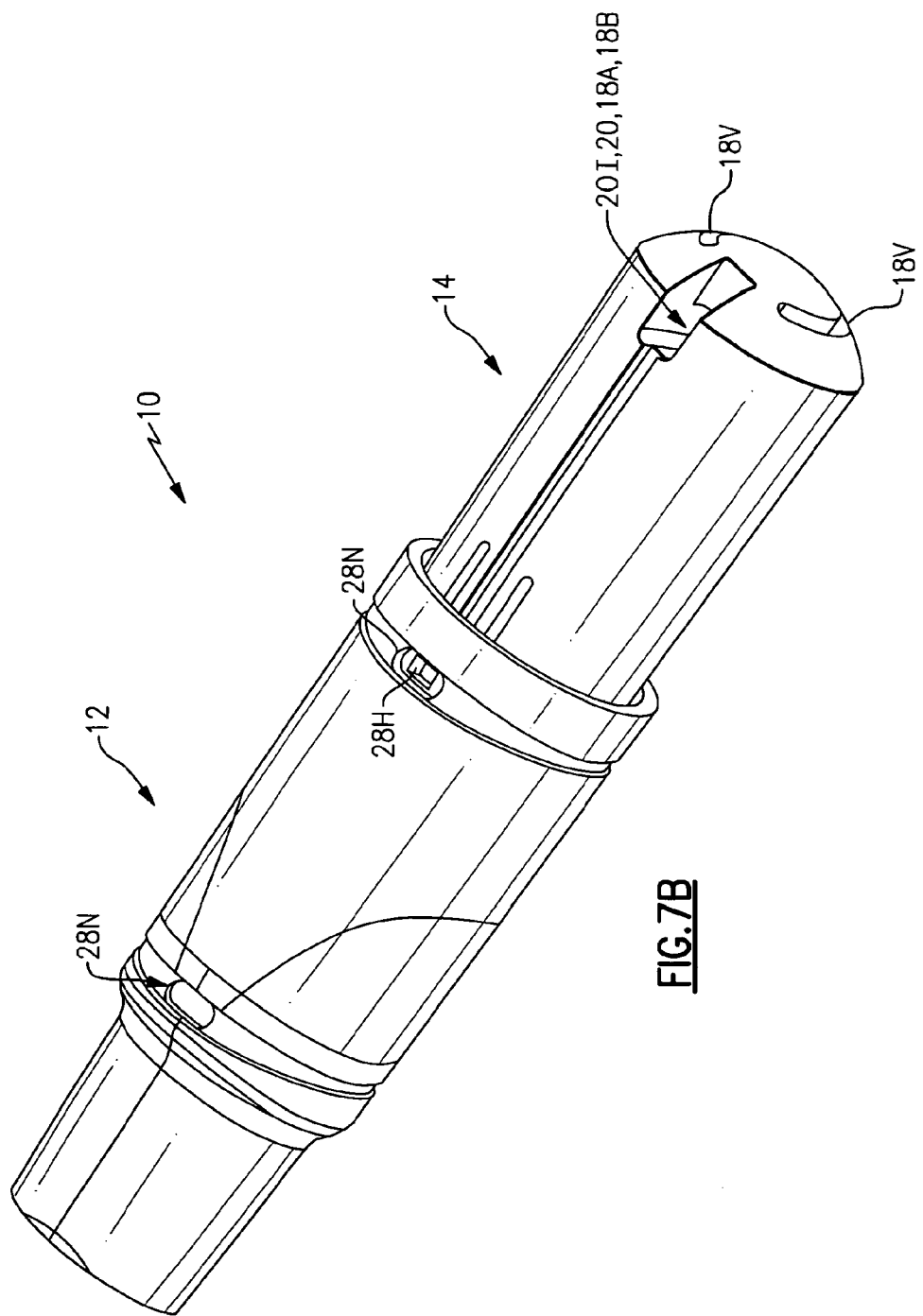

In a typical implementation, such as illustrated in FIGS. 7A-7D, for example, the needle 26 is approximately 1 inch long and 0.11 inches in diameter with an inner bore diameter of between approximately 0.08 to 0.09 inches. There are two air/medication ports 26AM located on diametrically opposite sides of the needle 26 and each air/medication port 26AM is approximately 0.15 inches long. It will also be noted that when the illustrated inhaler 10 is in the actuated state, that is, the mouthpiece 12 and the body 14 are forced together as far as possible so that the needle 26 penetrates the medication container 16 to the maximum extent possible, as discussed above, the air/medication ports 26AM are positioned such that a portion or part of their length is located so at to communicate with the interior cavity of the medication container 16 and a portion or part thereof is located outside the medication container 16. As discussed, air/medication ports 26AM thereby function as both the air inlets 26A and the medication inlets 26M and the configuration provides the optimum air flow rate and circulation pattern to pick and carry the medication, from the interior cavity of the medication container 16, into the needle 26 and subsequently to the patient through the needle 26 and the mouthpiece 12, is illustrated in FIG. 7A.

It will also be noted that the length of the needle 26 and the length of the container chamber 14B are selected so that puncture point 26P does not contact the lower end of container chamber 14B and so that the lower inner side of mouthpiece 12, through which the needle 26 passes, does not contact and inadvertently crush the container 16.

In addition, it must be noted that the opening formed by puncture plane 26PP, cutting across the diameter of the medication delivery needle 26 to form the puncture point 26P, the puncture edges 26E, the cutting edges 26EC and the anti-coring edges 26EA all combine to define and form the air inlet 26A that, like the lower portion of the air/medication ports 26AM, communicates with lower air passage 20 for receiving and supplying exterior air. Lastly in this regard, it should be noted that in this implementation, the lower air passage 20, connecting air/medication port 26AM and the air inlet 26A to a flow of the exterior air, comprises a single vertical air passage 18A and a single horizontal air passage 18B connecting with a slot-like air inlet opening 20I.

In addition, the body 14 includes one or more bypass vent passages 20V concentrically located in cylindrical wall 14C between container chamber 14B and the outer surface of the body 14 and having, in the present embodiment, arc-shaped cross sections. In the illustrated embodiment the lower ends of bypass vent passages 20V communicate with the exterior air through a single vent slot 18V while the upper ends of bypass vent passages 20V connect to and communicate with the mouthpiece chamber 12A via bypass vent ports 12V and bypass vent passages 10V. It should be noted that while bypass vent slots 18V and 10V are illustrated in this example as being arc-shaped, these vents may have any appropriate or desired shape and the location of the same may vary.

A primary function of bypass vent passages 20V is to enhance the flow of air and medication through the mouthpiece 12 and to provide an optimum flow of air and medication to the user of the inhaler 10. As discussed, the body 14 includes one or more bypass vent passages 20V located in cylindrical wall 14C surrounding container chamber 14B with the lower ends of the vent passages 20V connecting to and communicating with the exterior air through one or more bypass vent slots 18V. The upper ends of the vent passages 20V, in turn, communicate with vent ports 12V and vent passages 10V that extend through mouthpiece 12 between the mouthpiece 12 face abutting vent passages 20V in the body wall 14C and the mouthpiece chamber 12A. The bypass vent passages 20V, the vent passages 10V and the vent ports 12V thereby form an alternative airflow path for the supplemental exterior air through the body 14 and the mouthpiece 12 into the mouthpiece chamber 12A, e.g., the air bypasses the air mixing with the medication powder and flowing through the needle 36 and the medication container 16.

First considering the flow of air and medication in mouthpiece chamber 12A, the mouthpiece chamber 12A represents a significant increase in the airflow passage volume compared to the flow passage through medication container 16 and the needle passage 12C, thereby resulting in a drop in flow pressure and velocity as the medication/air flow from medication container 16 and the needle passage 12C and enters mouthpiece chamber 12A. The additional flow of air into mouthpiece chamber 12A, via the bypass vent passages 20V, the vent passages 10V and the vent ports 12V, however, assists with maintaining the flow rate per unit volume in the mouthpiece chamber 12A by increasing the volume of air flowing into and through mouthpiece chamber 12A, thereby assisting with maintaining the flow pressure and velocity of the combined air flow through mouthpiece chamber 12A.

In addition, it has been found that there is a range of air/mediation flow parameters, such as air flow volume, flow resistance through the inhaler 10, suction applied by the user to cause the flow of air and medication to the user and the time for delivery of the medication, that is optimum with regard to user comfort as well as efficient delivery of the medication to the user. That is, if the flow resistance through the inhaler 10 is too great, the user may not be able to exert sufficient suction or suction over a sufficient period of time so as to draw all of the medication from the medication container 16. If, however, the flow resistance is too low, the effect could be akin to "stepping on a step that isn't there" or the user could receive a sudden, excessive surge of powdered medication. The bypass vent passages 20V, however, permit the flow resistance of the inhaler, and thus the suction required of the user, and the volume of air and air and combined with medication flowing, and thus the period over which the medication is delivered, to be adjusted to the optimum combination for various users.

It must also be noted in this regard that the flow rate and flow resistance through the inhaler 10 represents the combined flow rates and resistances of the parallel flow paths through the vent passages 20V and the medication container 16/needle 26 and that the medication is contained only in the flow though container 16, needle 26 and the needle passage 12C. Given a desired inhaler 10 flow rate and resistance, therefore, the rate of delivery of the medication and the period during which the medication is delivered to the patient is determined by apportionment of the combined flow rate through the inhaler 10 between the two flow paths, which thereby determines the flow rates and resistances through the two paths.

In a presently preferred implementation of the inhaler 10 using the needle 26 and having bypass vents, for example, the presently preferred ratio of the air-bypass flow rate to the needle flow rate is approximately of 75% to 25%, respectively, with a pressure drop through the inhaler 10 of being approximately 0.3 PSI at 28 l/min or 4 KPa at 25 l/min, which provides a very comfortable inhalation resistance for a patient or a user. The possible range of ratios of air-bypass flow rates to needle flow rates could, however and for example, be as high as 0% air flow through the bypass and 100% air flow through the needle, which would increase the airflow resistance to the patient but would also increase the medication flow rate and delivered volume of medication. In theory, the ratio of air-bypass flow to needle flow could be between from 0%-100% bypass to needle air flow to about 80%-20% bypass air flow to needle air flow. It has been found by experiment, however, that bypass/needle flow ratios of less than 20% of the flow through the needle results in dosage deliveries that are flow rate dependent while bypass/needle flow ratios of greater than 20% through the needle tends to provide dosage deliveries that are significantly less dependent on the flow rates. The bypass vent passages 20V assist with extraction of the medication from the medication container 16, through the needle 26 and the mouthpiece 12, by increasing the airflow through mouthpiece 12 to, in turn, create a suction effect to draw increased air flow through the medication container 16 and the needle 26.

Referring next to FIGS. 8A-8D, illustrated therein are an alternate embodiment of the medication delivery needle 26, designated as a pyramidal point medication delivery needle 36. As shown, a pyramidal delivery needle 36 comprises of a hollow tubular body 36B having a lower end terminated and closed by a solid tip comprising a pyramidal puncture point 36PP and at least one air/medication port 36AM. As shown in FIG. 8B, air/medication port or ports 36AM are located along the body 36B of the needle 36 so that when the illustrated inhaler 10 is in the fully actuated state, that is, the mouthpiece 12 and the body 14 are forced or pushed together so that the needle 36 penetrates the medication container 16 to the maximum extent, the air/medication port or ports 36AM are located primarily within the medication container 16 but also partially outside the medication container 16 so as to communicate with the lower air passage 20. For example, when the inhaler 10 is fully actuated, the port or ports 36AM may be located such that approximately 9/10ths of the port or ports are located within the medication container 16 and approximately 1/10th of the port or ports 36AM extending out of the medication container 16 and communicate with the lower air passage 20. It will, therefore, be apparent that according to the pyramidal needle 36, the pyramidal puncture point 36PP closes the leading end of the tubular body 36B so that the needle 36 does not have an air inlet 26A formed at the lower leading end of the needle 36 and so the air/medication port or ports 36AM of the needle 36 function as both air inlets 26A and medication inlets 26M of the needle 36, in a manner analogous to the air/medication ports 26AM of the needle 26.

As illustrated in FIGS. 8A-8D, the pyramidal puncture point 36PP may assume the form of, for example, a three or four sided pyramid with the tip of the pyramid, which forms the point for puncturing the medication container 16 when the inhaler 10 is actuated, being located along the central longitudinal axis or centerline of the needle 36 and thereby along the central longitudinal axis or centerline of the medication container 16. Comparison with the puncture point of the needle 26 as shown, for example, in FIG. 2F, will show that rather than cutting a single large flap 16BF of container material 16BM when penetrating the wall of the medication container 16, as in the case of the needle 26, the pyramidal puncture point 36PP will form openings bounded by three or four smaller flaps being formed in the walls of the medication container 16, depending on the number of faces formed in the tip of the pyramid.

It is anticipated that the use of the pyramidal puncture point 36PP will reduce the probability of material breaking or being ripped off from the container wall of the medication container 16 and possibly blocking transport of the medication and the air from the medication container 16 to the patient or being inhaled by the patient together with inhalation of the medication. It will be recognized, however, that the choice of the needle 26 or the needle 36, for any given inhaler 10, will often be determined by the dimensions and material or materials forming the medication container 16, and that either needle design may be advantageous under certain circumstances.

Lastly in this regard, it will be noted that the pyramidal needle 36, illustrated in FIGS. 8C and 8D, comprises a hollow, tubular body 36B and a separate pyramidal point 36PP that closes the leading end of the body 36B. It will be recognized, however, that the pyramidal needle 36 may be manufactured in a number of alternate ways, including as a pyramidal needle 36 wherein the body 36B and the pyramidal point 36PP are formed as a single unitary needle from a single piece of material. For example, a needle 36 may be manufactured by an injection molding process or by a plating molding process wherein a material is plated or otherwise deposited on a mold form. In another example, a single part needle 36 may be fabricated by a process wherein the needle 36 is initially manufactured as a hollow tube with the leading lower end of the tube being subsequently "notched" into three or four "petals" or triangles that are then crimped or squeezed together to form the pyramidal point 36PP.

Referring to FIG. 8E, therein is illustrated a yet further embodiment of an inhaler 10 with a yet further alternate embodiment of the medication delivery needle 26, designated as a double medication delivery needle 26XY comprising an upper delivery needle 26X and a lower delivery needle 26Y. As illustrated therein, the lower end of needle passage 12C, that is, the end of needle passage 12C ending at body chamber 12B, terminates in upper delivery needle 26X wherein upper delivery needle 26X extends into body chamber 12B by a distance sufficient to penetrate into and through the upper end of the medication container 16 when the inhaler 10 is activated, as described herein above. The upper needle 26X may assume any of the needle forms described herein above, such as those illustrated in FIGS. 1B and 8A, and will include an air and medication passage extending through the upper needle 26X to the lower end of the upper needle 26X and terminate in one or more inlets 26M located at the lower end of the upper needle 26X. Upper needle 26X need not necessarily include one or more air/medication ports 26AM but, however, may do so.

As also illustrated, the lower end of mouthpiece 12 further includes a container support/guide 12D that extends into upper chamber 12B around upper needle 26X to facilitate receiving, guiding and supporting the upper end of the medication container 16 during activation of the inhaler 10, when the mouthpiece 12 and the body 14 are axially moved or telescoped so that double needle 26XY respectively penetrates the opposed ends of the medication container 16. In an embodiment illustrated in FIG. 8E, the lower surface of container support/guide 12D forms a concave surface shaped at least generally to match the shape of the lower end of the medication container 16. The container support/guide 12D and, in particular, the outer rim portion of the container support/guide 12D, extends into upper chamber 12B by a distance sufficient to support and guide the medication container 16 during the inhaler 10 activation operation, and the length and the shape of the container support/guide 12D is such that it does not to interfere with the body 14 when the inhaler 10 is activated. In this regard, it will be noted that in the illustrated embodiment, the outer diameter of container support/guide 12D is sufficiently large to enclose at least a significant portion of the upper end of the medication container 16. The outer diameter of container support/guide 12D is less than the inner diameter of the upper chamber 12B in the illustrated embodiment, however, to allow a corresponding portion of the body 14 to extend into and interlock with the mouthpiece 12 in this space, in a manner similar to that illustrated with respect to FIG. 1A. In other embodiments, however, and for example, the container support/guide 12D may extend the full width of upper chamber 12D and the length of the container support/guide 12D may be such that there will not be interference between the mouthpiece 12 and the body 14 when the inhaler 10 is activated.

The lower needle 26Y, in turn, communicates with and terminates lower air passages 18A and 20 and extends upward into body chamber 12A by a distance sufficient to penetrate through the lower end of medication container 16 and communicate with the interior cavity of when the inhaler 10 is activated, as described herein above. Again, the lower needle 26Y may assume any of the needle forms described herein above, such as those illustrated in FIGS. 1B and 8A, and will include an air and/or medication passage extending through the lower needle 26Y which terminates in one or more outlets 26M located at the upper end of lower needle 26Y. Also again, the lower needle 26Y need not necessarily include one or more air/medication ports 26AM, but may do so.

Figure 8E:
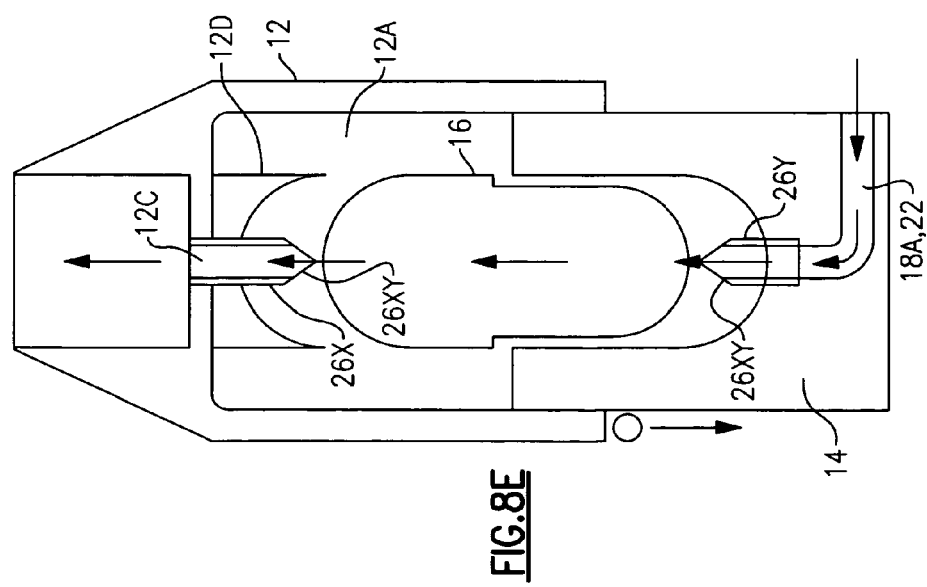

Lastly, it will be recognized that when the inhaler 10, illustrated in FIG. 8E, is activated by axially telescoping the mouthpiece 12 and the body 14, the upper and the lower needles 26X and 26Y will pierce opposed ends of the enclosed medication container 16 to form generally the same air/medication passage through the container 16 to the patient as was described above with respect to other forms of the needle 26, 36. In this regard, it will be recognized that the implementation illustrated in FIG. 8E differs essentially in that the middle section or region of the air/medication passage, through the medication container 16, comprises the medication container 16 itself rather than of the body of the needle 26, 36. It will also be recognized that the implementation shown in FIG. 8E allows a simpler needle 26XY because the needle comprises two short needles rather than a single longer and thus a possibly mechanically weaker needle. In addition, the use of two shorter needles reduces the requirements for alignment of the needle or needles because each of needles 26X and 26Y needs only to be generally aligned with the central longitudinal axis of the container 16 and chambers 14a and 14B. In implementations using a longer single needle, however, the needle must be generally aligned along the entire length of chambers 14A and 14B and the medication container 16 so as to penetrate the lower end of the medication container 16 and enter the lower air passage to communicate therewith.

D. Alternate Embodiments

Windowed Inhalers 10

Figure 9A:
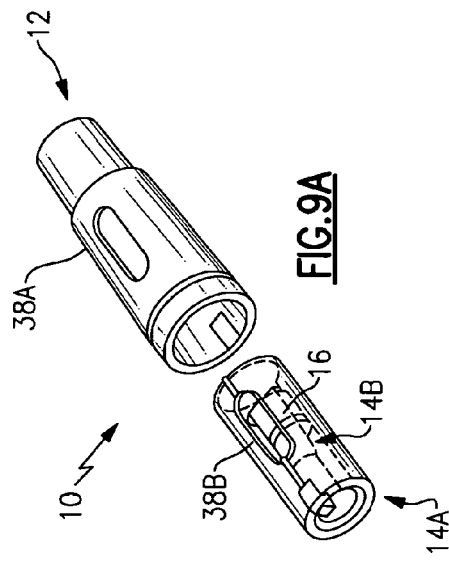
FIGS. 9A and 9B illustrate an inhaler having a container window(s)
Figure 9B:
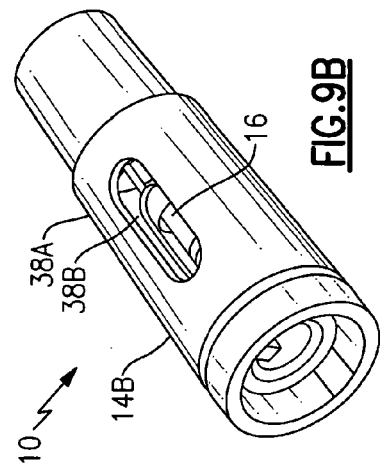

Referring to FIGS. 9A and 9B, therein are illustrated an embodiment of an inhaler 10 having container windows 38A and 38B in, respectively, the side walls of the mouthpiece 12 and the body 14 to allow visual inspection of the existence and state of the medication container 16 residing within the chamber 14B of the body 14. The mouthpiece 12 and the body 14 may have two diametric pairs of overlapping of windows 38A and 38B, one diametric pair located in the mouthpiece 12 and the other diametric pair in the body 14 with each pair being diametrically opposite one another, or may have a single pair of overlapping windows 38A and 38B located only on one side of the mouthpiece 12 and the body 14. The latter embodiment may require that the body 14, or the body 14 and the mouthpiece 12, comprise, for example, a transparent or translucent material, to allow sufficient light to enter the chamber 14B to illuminate the medication container 16 therein, or that the body 14 and the mouthpiece 12 have a light port located opposite the windows 38A and 38B for the same purpose.

It will be noted that in the embodiment specifically illustrated in FIGS. 9A and 9B, the container window or windows 38B in body 14 are located directly adjacent chamber 14B and are of a length sufficient to allow a adequate viewing of the medication container 16 in the chamber 14B. It will also be noted that in this embodiment, the window or windows 38A in the mouthpiece 12 are located so as to be directly adjacent the window or windows 38B when the inhaler 10 is actuated, that is, when the body 14 has is received by the mouthpiece 12 so that the medication can be released to the patient. This arrangement will allow visual inspection of the actuated inhaler 10 to provide an indication of whether there was a medication container 16 within the inhaler 10 and whether, or to what extent, the medication therein has been delivered to the patient.

It may also be desirable to allow inspection of, for example, a pre-loaded but not yet actuated inhaler 10, such as an inhaler 10 that has been stored in the pre-loaded state, which would allow viewing of the chamber 14B while the mouthpiece 12 and the body 14 were in the non-actuated position. This may be accomplished, for example, by designing the body 14 and the mouthpiece 12 so that at least a portion of the window 38B and the chamber 14B extend outside the mouthpiece 12 when the inhaler 10 is in the non-actuated position. In other embodiments, such as embodiments wherein chamber 14B is enclosed within the mouthpiece 12 in the assembled and loaded state but while in the non-actuated position, the window 38A in the mouthpiece 12 may be extended to overlap the window 38B in the body 14 when body 14 is in the non-actuated position. Alternately, the mouthpiece 12 may be provided with two axially spaced windows, one located to correspond with window 38B when the body 14 is in the non-actuated position and the other located to correspond with window 38B when the body 14 is in the actuated position.

It should also be noted that windows 38A and 38B comprise a passage through the walls of the mouthpiece 12 and the body 14 and into the chamber 14B, which may raise questions of preventing loss of the medication through the windows 38B and 38A or of an unwanted flow of air into the chamber 14B through the windows. This issue, however, may be addressed in a number of ways, such as adequately sealing the window 38B through the wall of the chamber 14B with a transparent or translucent "window pane", using a medication container 16 of dimensions and material suitable to provide and preserve the sealing of the chamber 14B, or manufacturing the body 14 of a transparent or a sufficiently translucent material that will allow light to pass therethrough while still providing a sealed chamber 14B.

E. Alternate Embodiments

Multiple Dose Inhalers 10

As discussed elsewhere herein, the inhaler 10 may also be designed to contain and deliver multiple medication dosages, thereby including a mechanism or structure for holding multiple medication containers 16 and to allow the selection and actuation of individual medication containers 16 as desired. The mechanism for holding and selecting among multiple medication containers may, for example, assume the form of a magazine or clip inserted into the body 14 (FIG. 10A), such as used to load cartridges into firearms, or the body 14 may itself contain multiple chambers 14B, similar to the chambers in a cylinder for a revolver (FIG. 10B). In the case of a magazine or clip mechanism, the entire clip or magazine could be provided with an overpack to provide the necessary shelf life for the medication, or each of the individual containers could be contained in an individual overpack. In the case of a revolver cylinder arrangement with multiple chambers 14B, it would be possible to provide each medication container 16 with an individual overpack, or the body 14 with the medication containers 16 therein could be provided with an comprehensive overpack. It will be recognized, in this regard, that those implementations of a clip or magazine or a body 14 with an overall overpack, as opposed to individual overpacks for the individual containers 16, it would be necessary to use all of the dosages of the "opened package" within the shelf life of the medication.

Figure 10A:
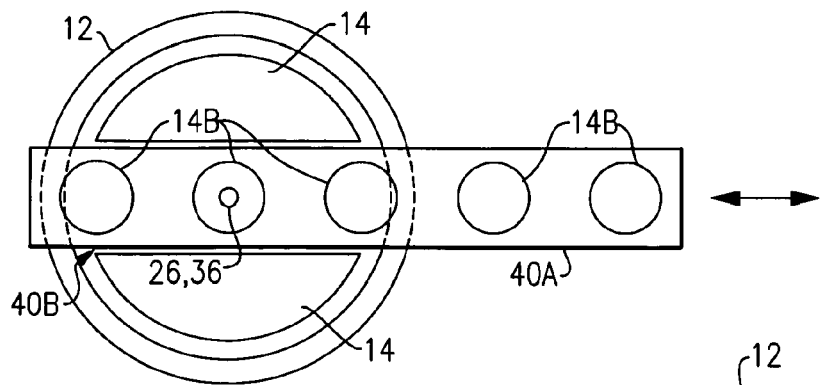
FIG. 10A is a diagrammatic end view illustration of an inhaler accepting a linear magazine containing multiple chambers and containers.
Figure 10B:
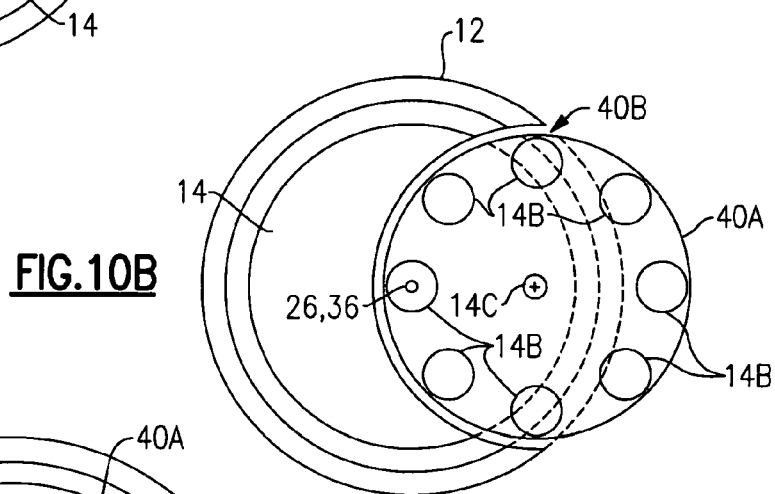
FIG. 10B is a diagrammatic end view illustration of an inhaler accepting a rotary magazine having multiple chambers and containers.

Examples of such embodiments of the inhaler 10 are illustrated in FIGS. 10A through 10D wherein FIG. 10A is a diagrammatic end view illustration of an inhaler 10 accepting a linear clip or magazine 40A containing multiple chambers 14B and corresponding medication containers 16. As shown therein, the mouthpiece 12 and the body 14 include a magazine slot 40B axially traversing the mouthpiece 12 and the body 14 at the axial location occupied by the chamber 14B in the previously described embodiments of the inhaler 10. That is, so that the needle 26, 36 does not contact the medication container 16 in the chamber 14B currently aligned with the needle 26, 36 when the body 14 is in the non-actuated position with respect to the mouthpiece 12 and so that the needle 26, 36 will penetrate the medication container 16 when the body 14 is moved to the actuated position with respect to the mouthpiece 12. As will be apparent from FIG. 10A, individual containers 16 may be selected and used in any order by sliding the magazine 40A, along magazine slot 40B, until the desired chamber 14B and associated medication container 16 are axially aligned with the needle 26, 36.

FIG. 10B is a diagrammatic end view illustration of an inhaler 10 generally similar to that of FIG. 10A except that magazine 40A is formed into a circular structure rotating about an offset longitudinal axis 40C, or axle, located, for example, one an outer rim of the body 14 and the magazine slot 40B is correspondingly shaped to accept and support the rotatable magazine 40A. In this embodiment, therefore, the magazine 40A is rotated, rather than slid linearly, to bring the desired chamber 14B and the associated medication container 16 into axial alignment with the needle 26, 36, thereby comprising a revolver cylinder type mechanism.

Figure 10C:
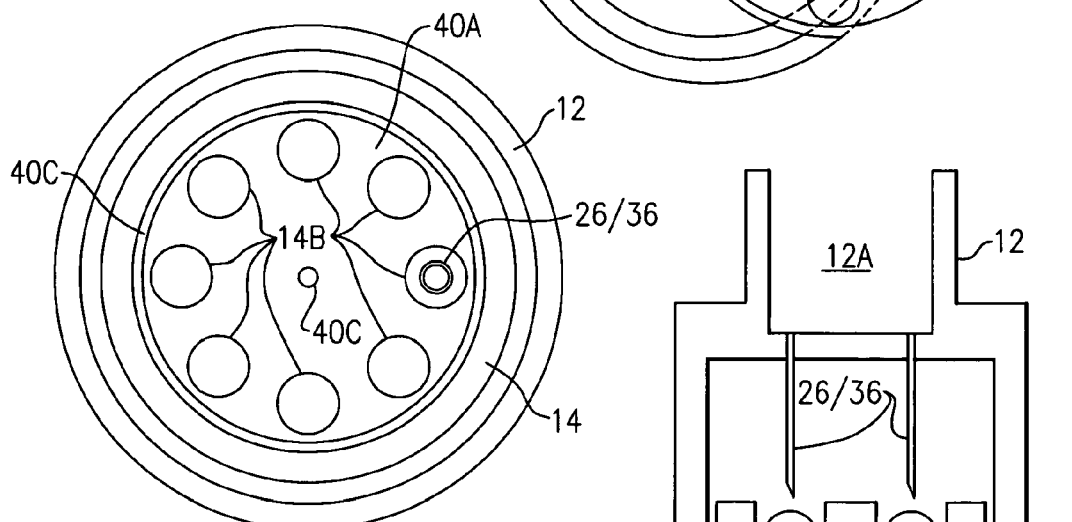
FIG. 10C is a diagrammatic end view illustration of an inhaler having a cylindrical magazine having multiple chambers and containers.

FIG. 10C is a diagrammatic end view illustration of an inhaler 10 having a cylinder-like magazine 40A wherein the magazine 40A rotates about a central axis 40C that is coaxial with the central longitudinal axis of the body 14 and the mouthpiece 12 so that the chambers 14B and the medication containers 16 therein rotate about the outer rim of the body 14. In this implementation, the needle 26, 36 and the air passages described herein above are offset toward the outer circumference of the body 14 and the mouthpiece 12 so that the desired chamber 14B and the associated medication container 16 therein are brought into alignment with the needle 26, 36 by rotation of the magazine 40A about the centrally located axis 40C. It will be noted that according to this implementation, the air/medication passage to and through the mouthpiece 12 will typically be directed or extend toward the periphery of the body 14, pass through the desired chamber 14B and the associated medication container 16 contained therein and thereafter be directed or extend toward and generally align with the central longitudinal axis of the mouthpiece 12 to thereby pass to the patient along the central longitudinal axis of the mouthpiece 12.

Figure 10D:
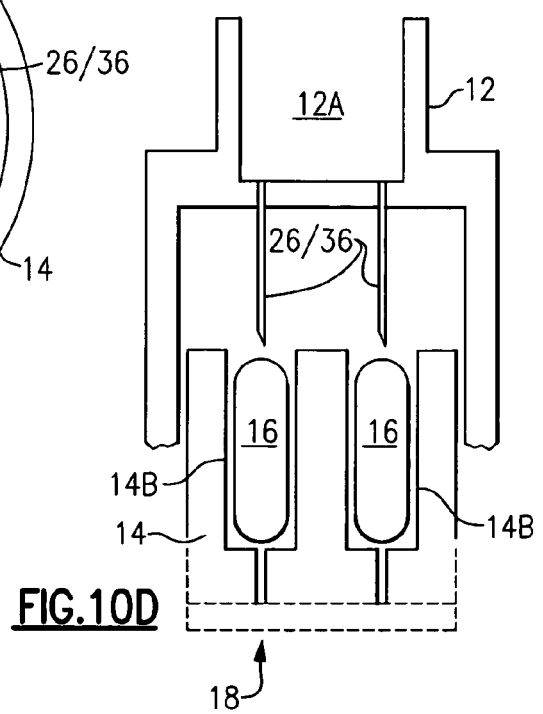
FIG. 10D is a diagrammatic side view illustration of a multiple medication inhaler.

Lastly, FIG. 10D is a diagrammatic side view illustration of a multiple medication inhaler 10 capable of simultaneously delivering a plurality dosages of medication(s) to a patient during a single actuation wherein the medications in the respective chambers 14B may be different from one another or may be the same medication. It will also be apparent that not all of the chambers 14B must contain medication therein at a given time and for a given actuation, but it may be preferable to "blank off" any unused chamber(s) 14B to control the air flow through the unused chamber(s) 14B, such as inserting or placing a "dummy" container(s) 16 or a plug(s) into any unused chamber(s) 14B prior to actuation.

As illustrated therein, the body 14 contains a plurality of container chambers 14B arrange in any manner to accommodate a respective number of medication containers 16 therein. The illustrated example includes two chambers 14B arranged in parallel, but it will be recognized that other embodiments may include a different number of chambers 14B arranged, for example, in a triangular pattern or a circle. As also shown, each individual container chamber 14B may have a separate individual air passage 18 for drawing exterior air into and through the chamber 14B and controlling the air flow therethrough or, in other embodiments, a common air passage 18 may then separate into a separate supply lines for supplying exterior air to each respective chamber 14B. The mouthpiece 12 of the multiple medication inhaler 10, in turn, will include a corresponding plurality of needles 26, 36 and air/medication passages connecting or coupling the chambers 14B with generally a single mouthpiece chamber 12A. This embodiment will also generally be provided with a bypass air flow (not shown in detail), to provide additional supplemental air to the patient.

As may be seen from FIG. 10D, therefore, actuation of the multiple medication inhaler 10 will result in the simultaneous opening of each of the medication containers 16 residing in the respective chambers 14B so that the patient will then concurrently receive medication from each one of the medication containers 16.

F. Alternate Embodiments

Detent Mechanisms

As discussed herein above, the inhaler 10 of the present invention may include a detent mechanism for retaining or holding the mouthpiece 12 and the body 14 in an "open" stored, non-actuated position until a user desires to activate the inhaler 10, thereby allowing the inhaler 10 to be preloaded and stored for subsequent use or to be handled safely after loading. Referring to the detent mechanisms 28H, 28N of the illustrated embodiment, it can be seen in FIGS. 6A-6B that the detent mechanisms 28H, 28N are embodied in a resiliently biased tooth and notch structure that includes opposing paired resiliently biased detent hooks 28H that engage with opposing pairs of detent notches 28N at least two locations along mouthpiece 12. As shown in FIGS. 6A and 6B, one pair of detent notches 28N is located at the position corresponding to detent hooks 28H when the inhaler 10 is in the stored state, that is, when the inhaler 10 is loaded with a medication container 16 and assembled, but not yet activated, to retain the body 14 in the stored, non-actuated position with respect to the mouthpiece 12. The second pair of detent notches 28N is located at the position corresponding to the location of detent hooks 28H when the inhaler 10 is in the fully activated state, that is, when the body 14 has been moved relative to and received by the mouthpiece 12 so that needle 36 pierces through the medication container 16 and provides access to the medication therein, for retaining the mouthpiece 12 and the body 14 in the fully activated state.

It must also be recognized with respect to detent mechanisms 28, however, that any of a wide range of detent or other types of conventional locking arrangements, which are well known in the arts, may be used in place of the illustrated arrangement without departing from the invention disclosed herein. For example, the detent mechanism 28 may comprise a bayonet type locking mechanism operating between the mouthpiece 12 and the body 14. In a further example, the detent mechanism 28 may comprise a threaded mechanism wherein matching and engaging portions of the mouthpiece 12 and the body 14 are correspondingly threaded so that rotation of one with respect to the other will draw the mouthpiece 12 and the body 14 into the activated state.

G. Alternate and Preferred Embodiments

Air And Powder Flow in an Inhaler and Alternate Needle Embodiments

The above descriptions have described and discussed various elements and combinations of elements comprising possible exemplary embodiments of the inhaler 10 according to the present invention. The following description will now describe and discuss various elements of the design of the inhaler 10 with regard to test results obtained from various configurations of those elements. The following will also discuss and describe optimization of the flow of air and powdered medication through the inhaler 10 for various configurations of the elements, and certain presently preferred combinations of those elements and the resulting presently preferred embodiments of the inhaler 10.

As will be noted from the following description that these further embodiments all use the medication delivery needle described herein above as a pyramidal point medication delivery needle 36. As described previously with respect to FIGS. 8A-8D, the pyramidal delivery needle 36 comprises a hollow tubular body 36HB having a lower end terminated and closed by a pyramidal puncture point 36PP and one or more air/medication port or ports 36AM being located along the body 36B of the needle 36. The air/medication ports 36AM are located along the length of the needle 36 so that when the illustrated inhaler 10 is in the actuated state, that is, the mouthpiece 12 and the body 14 are pushed for forced together so that needle 36 penetrates the medication container 16 to the maximum extent, the air/medication port or ports 36AM are located partially within the medication container 16 and partially outside the medication container 16 so as to communicate with the lower air passage 20. For example, when the inhaler 10 is fully actuated, the port or ports 36AM may be located with approximately 9/10ths of the port or ports being accommodated within the interior cavity of the medication container 16 and approximately 1/10th being located outside the medication container 16 and communicating with the lower air passage 20. In this embodiment, therefore, and because pyramidal puncture point 36PP closes the leading end of the tubular body 36B, the needle 36 does not have an air inlet 26A, at the leading lower end of the needle 36, and the air/medication port or ports 36AM of the needle 36 perform the functions of air inlets 26A and medication inlets 26M of the needle, as described above.

As also described previously, the pyramidal puncture point 36PP typically is a four sided pyramid with the tip of the pyramid, which forms the point for puncturing the medication container 16 when the inhaler 10 is actuated, being located along the central longitudinal axis of the needle 36 and the central longitudinal axis of the medication container 16. As described above, the pyramidal puncture point 36PP will form an opening through each opposed wall of the medication container 16 that is bounded by three or four small flaps, depending on the number of faces of the pyramid point.

A presently preferred embodiment of the inhaler 10 further include one or more bypass vent passages 20V as described with reference, for example, to FIG. 7C, for enhancing the flow of air and medication through the mouthpiece 12 and providing an optimum flow of air and medication to a user of the inhaler 10. As discussed, the body 14 includes one or more bypass vent passages 20V located in cylindrical wall 14C surrounding container chamber 14B with the lower ends of vent passages 20V communicating with the exterior air through one or more bypass vent slots 18V. The upper ends of vent passages 20V, in turn, connect with and communicate with vent ports 12V and vent passages 10V that extend through mouthpiece 12 between the mouthpiece 12 face abutting vent passages 20V in body wall 14C and the mouthpiece chamber 12A. The bypass vent passages 20V, the vent passages 10V and the vent ports 12V thereby form an air flow path for the exterior air through the body 14 and the mouthpiece 12 to the mouthpiece chamber 12A and bypassing the air and the medication powder flow path through needle 36 and the medication container 16.

First considering the flow of air and medication in mouthpiece chamber 12A, the mouthpiece chamber 12A represents a significant increase in the airflow passage volume compared to the flow passage through container 16 and the needle passage 12C, thereby resulting in a drop in flow pressure and velocity as the medication/air flow from the medication container 16 and the needle passage 12C enters mouthpiece chamber 12A. The additional flow of air into the mouthpiece chamber 12A, via the bypass vent passages 20V, the vent passages 10V and the vent ports 12V, however, assists with maintaining the flow rate per unit volume in the mouthpiece chamber 12A by increasing the volume of the air flowing into and through the mouthpiece chamber 12A, thereby assisting with maintaining the flow pressure and velocity of the combined air flow through mouthpiece chamber 12A.

In addition, it has been found that there is a range of air/mediation flow parameters, such as air flow volume, flow resistance through the inhaler 10, suction applied by the user to cause the flow of air and medication to the user and time for delivery of the medication, that is optimum with regard to user comfort and efficient delivery of the medication to the user. That is, if the flow resistance through the inhaler 10 is too great, the user may not be able to exert sufficient suction or exert suction over a sufficient period of time to draw all of the medication from the container 16. If, however, the flow resistance is too low, the effect could be akin to "stepping on a step that isn't there" or the user could receive a sudden, excessive surge of the powdered medication. The bypass vent passages 20V, however, permit the flow resistance of the inhaler, and thus the suction required by the user, and the volume of air and air and medication flowing to the user, and thus the period of time over which the medication is delivered, to be adjusted to the optimum combination for desired users.

It must also be noted in this regard that the flow rate and flow resistance through the inhaler 10 represents the combined flow rates and resistances of the parallel flow paths through vent passages 20V and the medication container 16 and the needle 36 and that the medication is contained only in the air flowing though the medication container 16, the needle 36 and the needle passage 12C. Given a desired inhaler 10 flow rate and resistance, therefore, the rate of delivery of the medication and the period during which the medication is delivered is determined by apportionment of the combined flow rate through the inhaler 10 between the two separate flow paths, which thereby determines the flow rates and resistances through the two respective flow paths.

In a presently preferred implementation of the inhaler 10 using a needle 36 and having bypass vents, for example, the air-bypass flow rate to needle flow rate is approximately 75% to 25%, respectively, with a pressure drop through the inhaler 10 of approximately 0.3 PSI at 28 l/min or 4 KPa at 25 l/min, which provides a very comfortable inhalation resistance for patients. The possible range of ratios of air-bypass flow rates to needle flow rates could, however, vary depending upon the application at hand. For example, the air-bypass flow rate could approach 0% while the needle flow rate could approach 100% and such parameters would increase the airflow resistance to the patient but would also increase the medication flow rate and delivered volume of medication to the patient and the inhaled dose. In theory, the ratio of the air-bypass flow to the needle flow rate could range from about 0%-100% to about 80%-20%. It has been found by experiment, however, that flow rates through the needle less than 20% results in dosage deliveries that are flow rate dependent while flow rates through the needle greater than 20% tends to provide dosage deliveries that are significantly less dependent on the flow rates.

Having consider the elements common to the range of the presently preferred embodiments of the inhaler 10, that is, the use of a pyramidally pointed needle 36 in combination with suitable bypass vent passages 20V for supplying additional air to the patient, the following will now consider other features and alternatives with reference to FIGS. 11A-11C, 12-17, and 18A-18D. The following will also describe the results of tests performed with various needle 36 implementations and variations thereof.

Figure 11A:
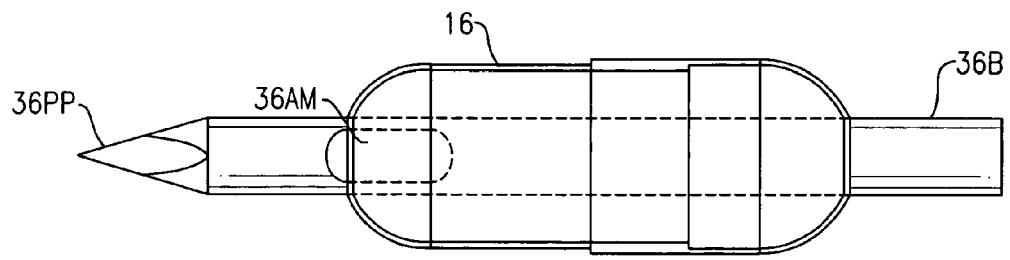
FIG. 11A is a diagrammatic illustration of a basic pyramidal pointed medication delivery needle.
Figure 11B:
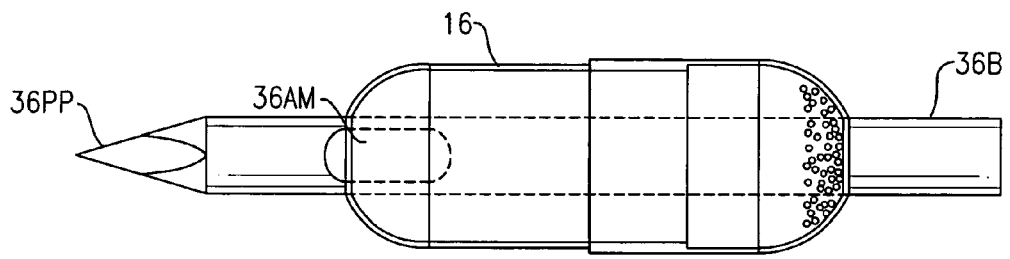
FIG. 11B is an illustration of the impaction and trapping of medication powder in a "dead zone" of a basic needle configuration.

First considering the operation of a basic pyramidal delivery needle 36, FIG. 11 illustrates a pyramidal needle 36 comprising a hollow tubular body 36B which terminates as a pyramidal puncture point 36PP. The pyramidal needle 36 has two air/medication ports 36AM located on opposite sides of the body 36B and spaced from the pyramidal puncture point 36PP. As shown, air/medication ports 36AM are located along body 36B of the needle 36 so that after the needle 36 has fully penetrated the medication container 16, approximately 9/10ths of the cross-sectional open area of air/medication ports 36AM is accommodated within and communicates with the medication container 16 while approximately 1/10th of the cross-sectional open area of air/medication ports 36AM communicates with the lower air passage 20. Experiments have found that the basic pyramidal delivery needle 36, as illustrated in FIG. 11A, provides excellent air/powder circulation within the medication container 16, causing good de-agglomeration of the medication particles by operation of vortex shearing and particle-to-particle and particle-to-needle collisions. This basic needle arrangement typically delivers approximately 71% of the powdered medication, contained in the medication container 16, within approximately 750 ms, occasionally leaving behind a small amount of impacted medication powder at a point in the medication container 16 directly around the area of the initial needle entry opening into the medication container 16, as illustrated in FIG. 11B. The average emitted dose of the Irvine needle was typically around 71-77%.

Figure 11C:
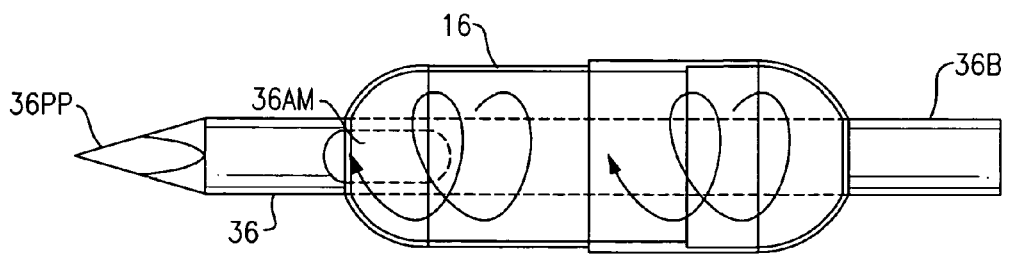
FIG. 11C is an illustration of the formation of vortices in the air and powder flow in a basic needle configuration.

The circulation of air and powdered medication, within the medication container 16, is apparently is caused and driven by a rotational vortex that forms above one of the pair of opposing air/medication ports 36AM formed in the needle 36, as illustrated in FIG. 11C. Current evidence indicates that because of variations in the initial puncturing of the medication container 16, one air/medication port 36AM typically has slightly more area exposed outside of the medication container 16, that is, communicates with the lower air passage 20, while the opposite air/medication port 36AM has more area exposed within the medication container 16. The resulting imbalance in pressures, at the air/mediation ports 36AM, results in one air/medication port 36AM becoming primarily an inlet vent from needle 36 and into the medication container 16 and the other air/medication port 36AM becoming primarily an outlet vent from the container 16 and into the interior passage of the needle 36. The air/medication port 36AM, functioning primarily as an outlet vent, drains the medication container 16 of powder by forming a stable rotational vortex above its outlet vent air/medication port 36, as illustrated in FIG. 11C, and this vortex induces other sympathetic, stable, vortices within the remainder of the medication container 16. As is typical with free vortices, radial variation of vorticity causes concentric shear planes within the vortex and larger particles of the powdered medication tend to have sufficient momentum to escape these vortices and collide with other particles thereby causing de-agglomeration of the larger particles, provided they do not impact on the walls of the medication container 16. Further pressure gradients between the inlet and outlet vents, formed by air/medication ports 36AM, have also been observed to accelerate some particles in concentric paths around the needle.

It was noted that the penetration of the needle 36 into the medication container 16 resulted in small openings between the wall of the medication container and the wall of the needle 36 at the entry end of the container 36, that is, at the end of the medication container 16 initially penetrated by the needle 36 and at which some accumulation of medication particles was observed. It was unclear, however, to what extent these small openings contributed to the airflow within the capsule. For example, some particles appeared to travel towards a rear end of the medication container 16, turn, and accelerate out in an elliptical path, but whether this was caused by venting from the small openings at the rear of the medication container 16 or from induced vortices could not be determined. As a result, a needle variant, having small openings at the rear end of the medication container 16, that is, at the end of the medication container 16 initially penetrated by the needle 36, was developed to study the effects of possible venting at the rear of the medication container 16, and this needle variant will be discussed in a following description.

Lastly, with regard to the basic form of the needle 36, it has been found that it is necessary that the air/medication ports 36AM be located sufficiently forward toward the tip or leading end of the needle 36 to insure that an adequate proportion of one or both air/medication ports 36AM extends completely through and out of the medication container 16 and thus communicates with the lower air passage 20. If, for example, the air/medication ports 36AM do not extend sufficiently through and out of the medication container 16, there is a risk that a "chad" or flap of the medication container wall, pushed outward by the penetration of the needle 36, may obstruct and/or block one or both of the air/medication ports 36AM to an unacceptable extent. The blockage of one or both air/mediation ports 36AM will unacceptably limit the flow of air from the lower air passage 20 into the needle 36 and prevent an adequate dispensing of the medication contained within the medication container 16.

In addition, the tip of the needle 36 must not extend so far past the end of the container 16 that the tip of the needle 36 engages with the end of container chamber 14B as this may, for example, prevent the proper actuation of the body 14 and the mouthpiece 12 or distort the relationship between the needle 36 and the medication container 16 by, for example, bending, tilting or otherwise distorting the needle 36.

Next, it will be noted that in the embodiment of the needle 36 illustrated in FIG. 11, for example, the penetration of the end wall of the medication container 16, by the pyramidal puncture point 36PP, results in the creation of four "flaps" of container wall material. The flaps remain attached generally to a perimeter edge of the penetration hole and are rotationally oriented with respect to the pyramidal puncture point 36PP so that the flaps are generally aligned with the faces of the pyramid and are separated along lines that are aligned with the vertices, or lines of joining, between adjoining faces of the pyramid. In the embodiment of the needle 36 illustrated in FIGS. 11A-11C, the four faced pyramidal puncture point 36PP is oriented with respect to the hollow tubular body 36B so that two opposing faces of the pyramid are aligned with the two opposing air/medication ports 36AM. This rotational orientation of the pyramidal puncture point 36PP thereby results in creating four flaps, when the point 36PP pierces the end wall of the medication container 16, with two of these flaps being generally aligned with the air/medication ports 36AM. This may result in the possibility that these two flaps could at least partially block or otherwise obstruct or restrict the flow of air into the air/medication ports 36AM.

Figure 12:
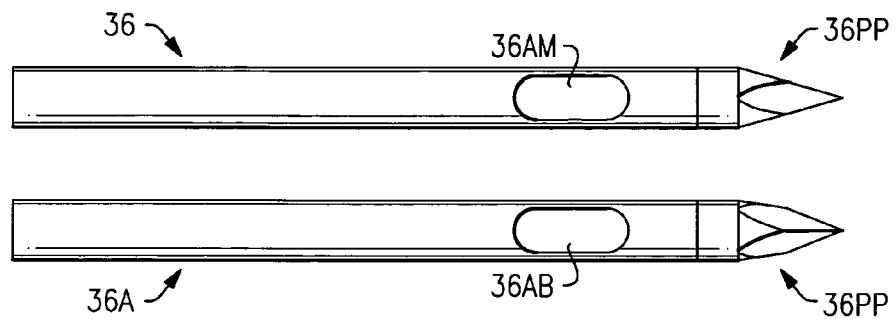
FIG. 12 are diagrammatic illustrations showing two basic configuration pyramidal point needles having tip vertices aligned with the air/medication ports.

For this reason, and as illustrated by the bottom needle 36A of FIG. 12 (the needle of FIGS. 11A-C is illustrated as the upper needle 36 in FIG. 12), a variant of the needle 36A was developed wherein the pyramidal puncture point 36PP is rotated 90° with respect to the orientation of the tip of FIG. 11 so that the vertices, between the flat faces of the pyramidal puncture point 36PP, are aligned with the air/medication ports 36AM, thereby reducing the potential for actual interference of the flaps of the medication container wall material with the flow of air into the air/mediation ports 36AM. It was found that this design resulted in somewhat stronger vortexes than those achieved for the needle design of FIGS. 11A-11, and that the somewhat improved movement and rotation provided by the stronger vortexes provided higher de-agglomeration of the particles. It was also found, however, that the higher momentum imparted to the powder, by the stronger vortexes, caused somewhat more particles to impact on the container wall. The results, in terms of medication delivery and air flow, were found to be similar to that in the needle design of FIG. 11, but to provided somewhat greater consistency and less deviation in the delivery of medication coupled with a reduced percentage of delivery due to powder impaction.

Figure 13:
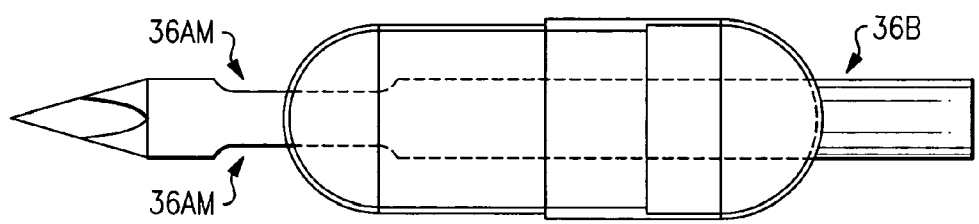
FIG. 13 is a diagrammatic illustration of a needle having longitudinally extended and shifted air/medication ports.

Referring now to FIG. 13, a second variant needle 36B is illustrated wherein the air/medication ports 36AM are longitudinally extended and repositioned or shifted toward the tip of needle 36B to increase the flow of air into the needle 36B from the lower air passage 20. As described previously with reference to FIGS. 7A-7D, an exemplary embodiment the needle 36B may be approximately 1 inch long and 0.11 inches in diameter with an inner bore diameter of between approximately 0.08 to 0.09 inches and each air/medication port 26AM is approximately 0.15 inches long. According to this variation of the needle 36B, again for example, air/medication ports 36AM may be lengthened by approximately 0.050 inches or so and moved toward the tip of needle 36B by approximately 0.010 inches or so. It was found that this variant of the needle 36B significantly improved the medication delivery rates and delivery percentages, which appears to be a direct consequence of the increased capability of drawing larger amounts of air into and through the needle at high velocity because of the larger exposed surface area of the air/medication ports 36AM located outside of the medication container 16 which can supply exterior air through from the lower air passage 20. Stated another way, if the total pressure of the system is conserved, according to the Bernoulli Equation, then increasing the dynamic pressure along a streamline by accelerating the flow will lower the static pressure of the fluid, which will cause a very low pressure in the medication container 16 and an increased draw of powder from the medication container 16. This is essentially an illustration of the Venturi Effect and, because of the velocities and speeds involved, it allows the medication container 16 to be substantially completely emptied at a very rapid rate.

Figure 14:
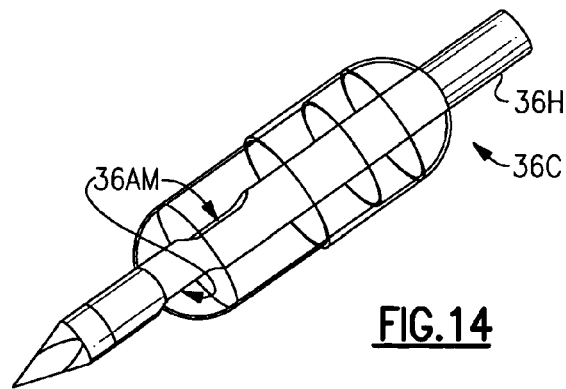
FIG. 14 is a diagrammatic illustration of a needle having asymmetrically located air/medication ports.

Referring to FIG. 14, a third variant needle 36C is illustrated wherein air/medication ports 36AM are asymmetrically located along the length of needle body 36B, with one port 36AM being located closer to the puncture point 36PP than the other to improve airflow consistency. In this configuration, the port 36AM closest to point 36PP is forced to function as an airflow input port allowing airflow into the container 16 from the lower air passage 20. At the same time, the rearmost port 36AM, that is, the port 36AM further from the point 36PP, is accommodated entirely within the medication container 16 and is thereby forced to function as an outlet for the flow of air and medication from the medication container 16 and into the interior passage of the needle 36C. This configuration was observed to result in the creation of a strong vortex over the rearward port 36AM, that is, the "container drain" port 36AM, and the creation of strong induced vortices in the rear portions of the medication container 16, that is, the regions of the medication container 16 around the initial penetration opening of the container. It was observed that vortices resulted in very high de-agglomeration of the medication particles through vortex shearing and particle collisions. It was also observed that in some instances the powder particles achieved sufficient momentum to escape the vortices and impact against and adhere to the walls of the medication container 16 and that, in some instances, there was an apparent "dead spot" located at the rear end of the medication container 16 due to a minimal or a lack of air circulation in that area or region. In most trials, however, the medication container 16 was substantially completely emptied of the particles of the medication powder.

Figure 15:
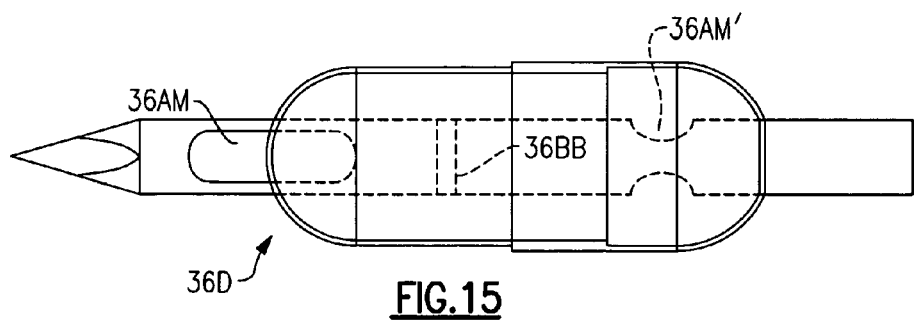
FIG. 15 is a diagrammatic illustration of a needle having forward and rearward pairs of air/medication ports separated by an internal baffle.

Referring to FIG. 15, a fourth variant needle 36D is illustrated therein that is "rear vented" by a second pair of air/medication ports 36AM' located toward the rear end of the needle 36D, that is, toward the end of the needle opposite the point 36PP of the needle 36D. The rear pair of ports 36AM' is in addition to the first pair of air/mediation ports 36AM located toward forward end of the needle 36D, that is, toward the end of needle 36D adjacent the point 36PP. An internal baffle 36BB is located between the first and the second pairs of air/medication ports 36AM, 36AM' and this baffle 36BB is accommodated within the interior medication container 16 following activation of the medication inhaler 10. The forward first pair of air/medication ports 36AM thereby functions as an airflow input port allowing airflow into the medication container 16 from the lower air passage 20 and the rearward second pair of air/medication ports 36AM functions as an outlet for the flow of air and medication from the medication container 16 and into the interior passage of the needle 36D. The resulting airflow path requires air to enter the medication container 16, via the forward pair of air/medication ports 36AM, and to traverse a portion of the length of the interior cavity of the medication container 16 before exiting via the needle 36D at the rear second pair of air/medication ports 36AM', thereby effectively eliminating airflow "dead spots" within the medication container 16. Tests shows that the medication particles in the medication container 16 were substantially completely evacuated within a very short period of time, on the order of about 350 msec, and that approximately 75% of the medication contained therein was consistently delivered to the patient. It was also observed that in some instances, the medication particles were drawn or swept toward the rear second pair of air/medication ports 36AM' with sufficient velocity to impact against and adhere to the rear end interior wall of the medication container 16.

Figure 16:
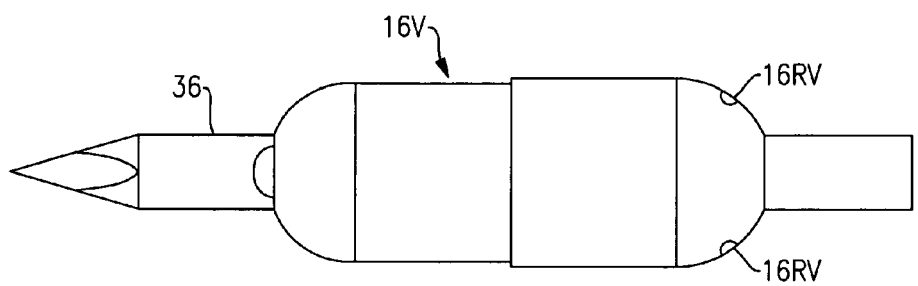
FIG. 16 is a diagrammatic illustration of a medication container having rear vent ports.

An alternate implementation of the medication container 16V, wherein the medication container 16 itself is rear vented to a flow of the exterior air, is illustrated in FIG. 16. As shown therein, the medication container 16V is vented by one or more vent holes 16RV formed through the rear wall of the medication container 16V, about a periphery of the rear end of the medication container 16V, that is, around the end of medication container 16V adjacent the end of the medication container 16 initially impacted by the needle 36. To achieve one or more vent holes 16RV, the mouthpiece 12 will generally carry one or more additional needles/vent ports which will pierce through the rear end of the medication container 16V and create the one or more vent holes 16RV therein, during actuation the inhaler. There vent holes 16RV will communicate with the exterior air, supplied by the bypass vent passages 20V, to supply additional air to the medication container 16V. This configuration of the medication container 16V was found by experiment to deliver over 76% of the medication particles to the patient within approximately 400 msec without any "dead spots" being formed within the medication container 16V.

Figure 17:
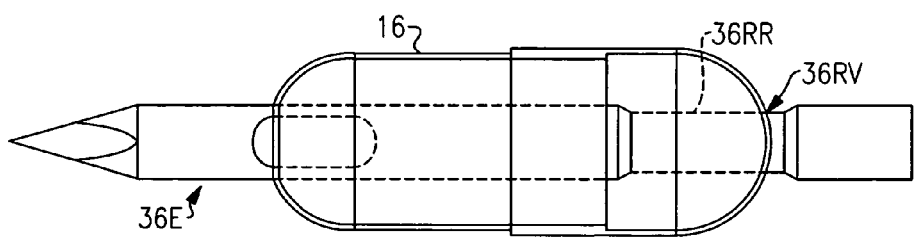
Figure 18B:
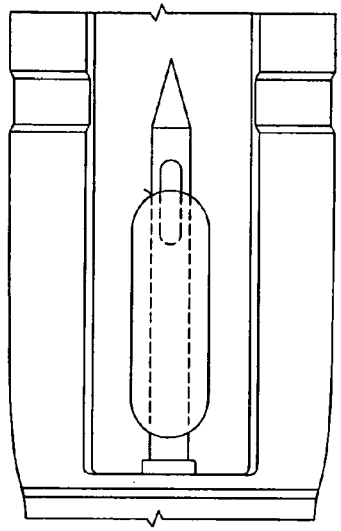
FIGS. 18A-18D are diagrammatic illustrations of centered and eccentric penetrations of a medication container by a needle.
Figure 18D:
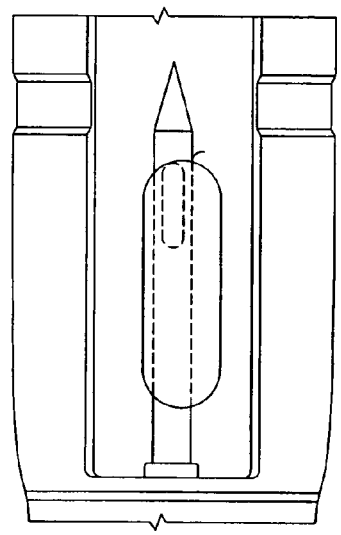
Figure 18A:
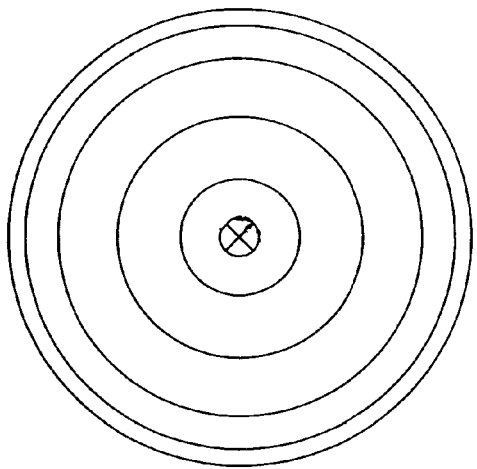
Figure 18C:
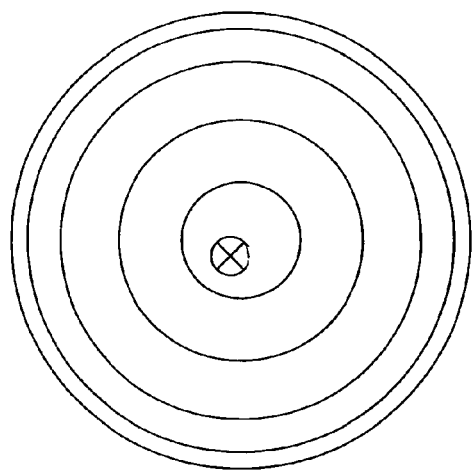

A further alternative embodiment of a rear vented needle 36E/container 16 structure is illustrated in FIG. 17. According to this variant, the exterior diameter of needle 36E is reduced at a trailing region 36RR that extends longitudinally between the interior and the exterior sides of the rear end wall of the medication container 16 when the inhaler 10 is in the actuated state. As has been illustrated herein above, penetration of the rear end wall of the container 16 by the needle 36E will result in an opening being formed through the end wall which will have a diameter approximately the same size as that of the needle 36E. The reduction in the exterior diameter of the needle 36E, in the trailing region 36RR, will thereby provide a small clearance between the exterior surface of the needle 36 and the inwardly facing surface of the medication container 16, i.e., form a rear vent passage 36RV therebetween to allow entry of additional air.

It has been shown the needle 36E configuration, as illustrated in FIG. 17, will result in a large pressure difference and a high air flow between rear vent passages 36RV and the air/medication ports 36AM located toward the tip end of the needle 36E. The resulting pressure gradient tends to carry substantially all of the medication powder particles from the rear end of the medication container 16 to the air/medication port 36AM located adjacent the forward end of the medication container 16 at high velocities, forming free vortices over the air/medication ports 36AM and drawing the medication particles into the internal passage of the needle 36E for conveyance to the mouthpiece 12. In some instances, the velocity of the airstream and the powder carried therein was sufficiently high to result in either permanent or temporary impaction of the powder against the opposite container wall. It was also found that rear vent passages 36RV resulted in less total air circulation throughout the container 16 and caused fewer particle collisions, and thus less de-agglomeration of the particles, because the vortices had less time to stabilize before the container 16 is substantially emptied of medication.

H. Container Alignment and Retention Issues

It was consistently observed during the above discussed tests and experiments, utilizing various configurations and implementations of the needles 36 and the medication containers 16, that off-center punctures and non-centered or eccentric positioning of the needle 36 when penetrating the medication containers 16 consistently resulted in inconsistent and reduced efficiency in the delivery of medication to the mouthpiece chamber 12C. It was also observed that off-center punctures and non-centered or eccentric punctures of the medication container 16 is generally due to the medication container 16 shifting or otherwise moving or distorting, during puncture of the container 16 by the needle 36, but may also be cause by shifting and/or distortion of the needle 36. These effects are illustrated in FIG. 18A-18D wherein FIGS. 18A and 18B respective illustrate end and side views of a desired center puncture of the medication container 16 by the needle 36 while FIGS. 18C and 18D respectively illustrate end and side views of a non-centered puncture of the medication container 16 by the needle 36.

Rigid control of the relationship between the medication container 16 and the needle 36 by rigidly holding and/or retaining the medication container 16 and the needle 36 in an aligned concentric orientation, i.e., the central longitudinal axes of both components being aligned with one another during activation of the inhaler 10, is therefore important in order to obtain a desired center puncture of the needle through the medication container 16 to maximize and optimize the delivery of medication.

I. Conclusions

The basic needle 36 configuration, as illustrated in FIGS. 11A-C, performed well and consistently with regard to emptying the medication from the medication container 16 and delivering the medication to the user as well as with in de-agglomerating substantially all of the medication powder in the examples tested. As described above, such configurations of needle 36, referred to as a pyramidal needle 36, comprise a hollow tubular body 36B which terminates in a pyramidal puncture point 36PP and has a pair of air/medication ports 36AM located on opposite sides of the body 36B in the region located adjacent the point 36PP. As discussed, the air/medication ports 36AM are located along body 36B of the needle 36 so that, once the needle 36 penetrates the medication container 16, approximately 9/10ths of the cross-sectional flow area of each air/medication port 36AM is accommodated within the medication container 16 while approximately 1/10th of the cross-sectional flow area of each air/medication port 36AM communicates with the lower air passage 20.

The various modifications, variants and alternate embodiments of needle 36, including the above discussed related modifications for the medication container 16, all resulted in one or more trade-offs of potential benefits and drawbacks. For example, extending and shifting the locations of the air/medication ports 36AM, as illustrated in FIG. 13, resulted in higher delivered dosages of the medication and venting of the medication container 16, either by means of vents in the medication container 16 or of rear vents formed by the overall configuration of the needle 36 outer contour, resulted in relatively complete and rapid emptying of the powder and relatively high delivered dosages. The increased airflow velocity, however, caused more impaction of the powder against the container wall, does not allow the vortices time to stabilize, and reduces the amount of time available to de-agglomerate the powder, all of which results in faster delivery of the medication but lower medication delivery percentages and greater inconsistency in the amount delivered.

The vertex-aligned needle tip configuration, as illustrated in FIG. 12, in turn provides better and more consistent airflow throughout the medication container 16, but the faster air flow causes slightly more impaction and adherence of the medication particles against and to the walls of the container and thereby reduced medication delivery.

The asymmetric needle configuration, illustrated in FIG. 14, yields much more consistent vortex formation. The vortex themselves were more intense and provided greater de-agglomeration, but the single inlet was observed to allow small dead spots in the rear of the capsule and the higher particle velocities caused some impaction and adhesion of medication particles against the walls of the container. The dead spots and volumes of impacted particles, however, were not significantly greater than those seen by the base configuration of the needle 36, as illustrated in FIG. 11

The results obtained with the needle 36 and the medication container 16 configurations, shown in FIGS. 15, 16 and 17, that is, needles 36 having forward and rearward sets of air/medication ports and an internal baffle or a circumferential rear vent formed between the needle and container wall and the rearwardly vented container, all provided similar test results. In particular, in each instance, the rate of flow of medication particles from the medication container 16 was notably increased, by approximately two times compared to the basic needle 36 configuration of FIG. 11. The higher flow rate and reduced medication extraction time, however, reduced vortex formation, thus reducing de-agglomeration of the mediation particles, and resulted in higher rates of particle impaction against the wall of the container, resulting in a higher percentage of trapped medication particles.

Lastly, the above described experiments included observation of the medication powder and air flow rates and patterns in the mouthpiece chamber 12C and it was consistently observed that the powder flow initialized as a focused jet emanating from the needle. It was further observed that within a few milliseconds the jet began to diffuse and turn back to circulate within mouthpiece chamber 12C, most probably due to a lower pressure adjacent the mouthpiece chamber 12C walls. It was also seen that there was little additional de-agglomeration of the medication particles within the needle itself, thereby indicating that the flow of air and powder within the needle is most probably laminar and non-rotating, e.g., irrotational.

It is desirable for the medication container chamber to have a very close and tight fit with the medication container once the medication container is received therein, e.g., a very small clearance, or possibly a slight interference fit, occurs between the exterior side wall of the medication container and the inwardly facing side surface of the medication container chamber. Such close and tight fit ensures that the central longitudinal axis of the medication container will be, and remain, substantially aligned and coincident with the central longitudinal axis of the medication container chamber, especially when the mouthpiece and the inhaler body are moved to the second activated position and the needle traverses the medication container contained within the medication container chamber. During such movement, the medication container has a tendency to become compressed and/or distorted as the needle commences piercing through the wall of the medication container. The close and tight fit, between the medication container and the medication container chamber, maintains medication container axially aligned with both the medication container chamber and the needle to facilitate desired piercing of the medication container substantially along its longitudinal axis, as described above, so that the needle, after passing through the medication container, will be aligned with the at least one air passage for coupling the medication container with the source of exterior air.

The bypass air, which is supplied to the mouthpiece chamber, facilitates ease of use of the medication inhaler by a patient. Although the above embodiments depicts the bypass air entering and passing, at least partially, though the inhaler body, it is to be appreciated that the mouthpiece may have one or more holes or openings therein, which directly communicate with the source of exterior air to facilitate suppling all, or a portion, of the bypass air to the mouthpiece chamber during use of the medication inhaler.

It is to be appreciated from the above discussion that the overall shape, size and/or design of the needle and the amount and the location of the air/medication ports provided in the needle can vary. The location and the amount of the air/medication ports are generally dictated by the type of medication to be dispensed from the medication container, e.g., the overall particle size range of the medication to be dispensed and the amount of turbulence and/or swirling pattern required to be generated within the medication container in order to facilitate substantially complete dispensing of the medication from the medication container.

It must be recognized with regard to the above description of possible implementations of the inhaler according to the invention that certain changes and adaption may be made in the above described improved medication inhaler, without departing from the spirit and scope of the invention herein involved. For example, while a presently preferred embodiment of the invention has been described and discussed in detail herein above, it must be recognized that different circumstances, such as medications have different particle sizes and/or characteristics, other features or combinations of features described herein above may result in an embodiment other than the exemplary embodiments described herein above. It is therefore intended that all of the subject matter of the above description or shown in the accompanying drawings shall be interpreted merely as examples illustrating the inventive concept herein and shall not be construed as limiting the invention.

What is claimed is:

1. A medication inhaler comprising:
   an inhaler body having
      a medication container chamber for receiving a medication container therein, and
      at least one air passage connecting the medication container chamber with exterior air, and
   a mouthpiece axially movable relative to the inhaler body and having
      a mouthpiece chamber for forming a passage between a patient's respiratory system and a hollow medication delivery needle,
      the hollow medication delivery needle communicating with the mouthpiece chamber and extending toward the medication container chamber and having at least one air/medication port for passing the exterior air and medication from an interior cavity of the medication container through the needle and to the mouthpiece chamber when the medication container is contained within the medication container chamber,
   wherein the mouthpiece engages with the inhaler body in
      a first position in which the needle extends into the medication container chamber short of the medication container, when the medication container is contained within the medication container chamber,
      in a second position in which the needle axially traverses the medication container so that the at least one air/medication port in the needle communicates with the at least one air passage and the interior cavity of the medication container in the medication container chamber; and
      the needle includes a hollow tubular body terminating in a puncture point formed by a solid tip leading end of the needle, and when the mouthpiece and the inhaler body are moved from the first position to the second position, the puncture point establishes an initial opening through a wall of the medication container such that material of the opening remains as a flap attached to a wall of the medication container, and
      the at least one air/medication port is located along the tubular body spaced apart from the solid tip and located in a side wall of the needle so that when the mouthpiece and the inhaler body are moved from the first position to the second position, the at least one air/medication port in the tubular body communicates with both the at least one air passage and the interior cavity of the medication container,
      the at least one air/medication port is located along the needle such that when the mouthpiece and the inhaler body are in the second position, a first portion of a length of the air/medication ports is located within the medication container and a second portion of the length of the air/medication ports is located outside of the medication container and communicates with the air passage connecting the medication container chamber with the exterior air; and
      the first portion of the length of the air/medication ports is greater than the second portion of the length of the air/medication ports.

2. The medication inhaler of claim 1, further comprising:
   a detent mechanism for retaining the mouthpiece and the inhaler body
      in the first position for storing the medication inhaler with the medication container loaded into the medication container chamber, and
      in the second position when the medication inhaler is actuated to deliver medication to the patient's respiratory system.

3. The medication inhaler of claim 1, wherein the pyramidal puncture point is located along a central longitudinal axis of the tubular body of the needle.

4. The medication inhaler of claim 3, wherein:
   the pyramidal puncture point includes a plurality of sides meeting at a pyramidal point, and
   penetration of the medication container wall, by the pyramidal puncture point of the needle, forms an opening through the medication container wall of approximately a diameter of the needle and bounded by corresponding flaps of the medication container wall material, with each flap of the medication container wall material corresponding to a face of the pyramidal point.

5. The medication inhaler of claim 1, further including:
   in the inhaler body,
      at least one body vent passage located between the medication container chamber and an outer surface of the inhaler body and connected to the exterior air, and
   in the mouthpiece, and
      at least one mouthpiece passage communicating between the at least one body vent passage and the mouthpiece chamber to provide a flow of exterior air into the mouthpiece chamber.

6. The medication inhaler of claim 5, wherein the mouthpiece further comprises:
   a medication container support/guide extending into the mouthpiece chamber for supporting the medication container when the mouthpiece and the inhaler body move from the first position to the second position.

7. The medication inhaler of claim 1, wherein the at least one air/medication port located along the medication needle comprises at least one pair of diametrically opposed air/medication ports.

8. The medication inhaler of claim 1, wherein the needle comprises:
   an upper needle extending from the mouthpiece chamber air passage and into the mouthpiece chamber, and
   a lower needle extending from the medication container chamber air passage and into the medication container chamber, wherein
   in the second position the upper and the lower needles respectively penetrate an upper and a lower surfaces of the medication container to form an air and medication passage between the medication container chamber air passage, the interior cavity of the medication container and the mouthpiece.

9. The medication inhaler of claim 1, wherein the medication container comprises one of:
   a capsule,
   a blister pack,
   a molded container, and
   a frangible pellet.

10. The medication inhaler of claim 1, further comprising:
    a container magazine having a plurality of medication chambers for each receiving a medication container therein, and
    a magazine slot in the inhaler body for receiving the container magazine, wherein
       the container magazine is adjustable within the magazine slot to selectively position at least one selected medication chamber and a medication container therein in alignment with the needle.

11. A multiple medication inhaler comprising:
    an inhaler body having
       a plurality of medication container chambers for each receiving at least one medication container therein, and
       at least one air passage for supplying each medication container chamber with a source of exterior air, and
    a mouthpiece axially movable relative to the inhaler body and having a mouthpiece chamber forming a passage between a patient's respiratory system and at least one of a plurality of hollow medication delivery needles,
       each of the plurality of hollow medication delivery needles communicating with the mouthpiece chamber, each needle extending toward a corresponding medication container chamber and having at least one air/medication port for supplying exterior air and medication from an interior cavity of the respective medication, container through the respective needle and to the mouthpiece chamber when the medication container is contained within the medication container chamber,
       wherein the mouthpiece engages with the inhaler body
          in a first position, in which the plurality of needles extend into the respective medication container chambers short of the medication containers in the medication container chambers, and
          in a second position in which each of the plurality of needles axially traverse a respective medication container so that the at least one air/medication port in the needle communicates with the at least one air passage and the interior cavity of the corresponding medication container;
          each needle includes a hollow tubular body terminating in a puncture point formed by a solid tip leading end of the needle, when the mouthpiece and the inhaler body are moved from the first position to the second position, the puncture point establishes an initial opening through a wall of the medication container such that material of the opening remains as a flap attached to a wall of the medication container, and
          the at least one air/medication port is located along the tubular body spaced apart from the solid tip and located in a side wall of the needle so that when the mouthpiece and the inhaler body are moved from the first position to the second position, the at least one air/medication port in the tubular body communicates with both the at least one air passage and the interior cavity of the medication container,
          the at least one air/medication port is located along the needle such that when the mouthpiece and the inhaler body are in the second position, a first portion of a length of the air/medication ports is located within the medication container and a second portion of the length of the air/medication ports is located outside of the medication container and communicates with the air passage connecting the medication container chamber with the exterior air; and
          the first portion of the length of the air/medication ports is greater than the second portion of the length of the air/medication ports.

12. A medication inhaler comprising:
    an inhaler body having
       a medication container chamber for receiving a medication container, and
       at least one air passage for supplying the medication container chamber with exterior air, and
    a mouthpiece axially movable relative to the inhaler body and having
       a mouthpiece chamber forming a passage between a patient's respiratory system and a hollow medication delivery needle,
       the hollow medication delivery needle communicating with the mouthpiece chamber and extending toward the medication container chamber and having at least one air/medication port for supplying exterior air and medication from an interior cavity of the medication container, in the medication container chamber, through the needle and to the mouthpiece chamber,
       wherein the mouthpiece engages with the inhaler body in
          a first position in which the needle extends toward the medication container chamber but is spaced from the medication container accommodated therein, and
          in a second position wherein the needle axially traverses the medication container so that the at least one air/medication port in the needle communicates with the at least one air passage and the interior cavity of the medication container in the medication container chamber,
       the needle having
          a hollow, tubular body,
          a pyramidal puncturing point closing a leading end of the tubular body, and
          when the mouthpiece and the inhaler body are moved from the first position to the second position, the puncture point establishes an initial opening through a wall of the medication container such that material of the opening remains as a flap attached to a wall of the medication container, and
          the at least one air/medication port comprises a pair of diametrically opposed air/medication ports located along the tubular body so that when the mouthpiece and inhaler body are moved from the first position to the second position, at least one of the diametrically opposed air/medication ports communicates with at least the at least one air passage and at least one of the diametrically opposed air/medication ports communicates with at least the interior cavity of the medication container, and
       at least one of the diametrically opposed air/medication ports is located along the needle such that when the mouthpiece and the inhaler body are in the second position, a first portion of a length of the at least one diametrically opposed air/medication ports is located within the medication container and a second portion of the length of the at least one diametrically opposed air/medication ports is located outside of the medication container and communicates with the air passage connecting the medication container chamber with the exterior air; and the first portion of the length of the at least one diametrically opposed air/medication ports is greater than the second portion of the length of the at least one diametrically opposed air/medication ports, the inhaler body and the mouthpiece including
at least one body vent passage located between the medication container chamber and an outer surface of the inhaler body and connected to the exterior air, and at least one mouthpiece passage communicating between the at least one body vent passage and the mouthpiece chamber to provide a flow of exterior air into the mouthpiece chamber.

13. The medication inhaler of claim 12, wherein diametrically opposed vertices of faces of the pyramidal puncturing point are longitudinally aligned with the pair of air/medication ports.

14. The medication inhaler of claim 12, wherein the air/medication ports are asymmetrically located along the tubular body of the needle.

15. The medication inhaler of claim 12, wherein the pair of diametrically opposed air/medication ports are a pair of forward air/medication ports located adjacent the puncturing point, and the needle further comprises:
a pair of rearward air/medication ports spaced from the pair of forward air/medication ports, and
a baffle is located within the tubular body between the pair of forward air/medication ports and the pair of rearward air medication ports.

16. The medication inhaler of claim 12, wherein the medication container includes at least one rear vent located at an end of the medication container opposite the puncturing point of the needle.

17. The medication inhaler of claim 12, wherein an exterior diameter of the needle located in a region extending inside and outside a rear wall of the medication container, when the mouthpiece engages with the inhaler body, has a reduced diameter to form a rear vent between an exterior diameter of the needle and the wall of the medication container surrounding an opening by which the needle entered the medication container.

* * * * *